US 8,287,888 B2

Oct. 16, 2012

(12) United States Patent
Song et al.

(10) Patent No.: US 8,287,888 B2
(45) Date of Patent: Oct. 16, 2012

(54) THERMOSENSITIVE POLYPHOSPHAZENE-BIOACTIVE MOLECULE CONJUGATES, PREPARATION METHOD THEREOF AND USE THEREOF

(75) Inventors: Soo-Chang Song, Namyangju (KR); Sun-Mi Lee, Busan (KR); Chang-Won Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 440 days.

(21) Appl. No.: 11/568,852

(22) PCT Filed: Nov. 3, 2006

(86) PCT No.: PCT/KR2006/004574

§ 371 (c)(1),
(2), (4) Date: Nov. 8, 2006

(87) PCT Pub. No.: WO2007/114549

PCT Pub. Date: Oct. 11, 2007

(65) Prior Publication Data

US 2009/0181088 A1 Jul. 16, 2009

(30) Foreign Application Priority Data

Apr. 4, 2006 (KR) .................. 10-2006-0030731
Nov. 1, 2006 (KR) .................. 10-2006-0107229

(51) Int. Cl.
*A61K 9/14* (2006.01)
*A61K 31/337* (2006.01)
*A61P 35/00* (2006.01)
(52) U.S. Cl. ............... 424/280.1; 424/484; 424/486
(58) Field of Classification Search .......... 528/337, 528/492
See application file for complete search history.

(56) References Cited

U.S. PATENT DOCUMENTS

| 5,149,543 | A | 9/1992 | Cohen et al. |
| 5,665,343 | A | 9/1997 | Sohn et al. |
| 5,914,231 | A | 6/1999 | Cohen et al. |
| 6,221,906 | B1 | 4/2001 | Sohn et al. |
| 6,319,984 | B1 | 11/2001 | Song et al. |
| 6,333,422 | B1 | 12/2001 | Sohn et al. |
| 6,951,953 | B2 | 10/2005 | Sohn et al. |
| 7,259,225 | B2 * | 8/2007 | Song et al. ............ 528/272 |
| 7,598,318 | B2 | 10/2009 | Sohn et al. |
| 2004/0219127 | A1 | 11/2004 | Sohn et al. |
| 2005/0020808 | A1 | 1/2005 | Song et al. |

FOREIGN PATENT DOCUMENTS

| JP | 06-505961 | 7/1994 |
| JP | 09-110996 | 4/1997 |
| JP | 11-501821 | 2/1999 |
| JP | 2002-540212 | 11/2002 |
| JP | 2003-514938 | 4/2003 |
| JP | 2004-506739 | 3/2004 |
| JP | 2006-089745 | 4/2006 |
| JP | 2006-525224 | 11/2006 |
| JP | 2006-528718 | 12/2006 |
| WO | WO9532736 | 12/1995 |
| WO | WO2004048431 | 6/2004 |

OTHER PUBLICATIONS

Sugahara et al., "Paclitaxel Delivery Systems: The use of amino acid linkers in the conjugation of paclitaxel with carboxymethyldextran to create prodrugs." Biol. Pharm. Bull. 2002:25(5);632-641.*

* cited by examiner

*Primary Examiner* — Walter Webb
(74) *Attorney, Agent, or Firm* — Lexyoume IP Meister, PLLC.

(57) ABSTRACT

The present invention relates to a poly(organophosphazene)-bioactive molecule conjugates in which biodegradable and thermosensitive poly(organophosphazene) with a functional group showing the sol-gel phase transition with change of temperature is combined with various bioactive molecules, such as drugs, a preparation method thereof, and a use thereof for delivery of bioactive molecules.

22 Claims, 4 Drawing Sheets at room temperature
(sol phase)

at body temperature
(gel phase)

THERMOSENSITIVE POLYPHOSPHAZENE-BIOACTIVE MOLECULE CONJUGATES, PREPARATION METHOD THEREOF AND USE THEREOF

BACKGROUND OF THE INVENTION (a) Field of the Invention

The present invention relates to poly(organophosphazene)-bioactive molecule conjugates in which biodegradable and thermosensitive poly(organophosphazene) with a functional group showing the sol-gel phase transition with change of temperature is combined with various bioactive molecules, such as drugs, a preparation method thereof, and a use thereof for delivery of bioactive molecules.

(b) Description of the Related Art

An aqueous solution of a thermosensitive polymer hydrogel can maintain sol-phase at low temperature, and can be changed into gel-phase by raising the temperature.

Such sol-gel phase transition can occur reversibly. Thermosensitive polymer hydrogel has been considered as a useful delivery material of drugs for injection due to its advantages that the aqueous solution thereof can be easily mixed with therapeutic drugs. Therefore, it can be easily injected into a living body without any surgical operation, and when injected into a desired region of a living body, it forms a gel-phase with a three-dimensional structure at body temperature and is thereby capable of controlled and sustained release of the drugs [Life Science, 65, 261 (1999); J. Control. Rel, 63, 155 (2000)].

However, a problem with drugs with small molecular weights or high hydrophilicity is that they can easily and rapidly pass through the three-dimensional network structure of the gel formed by the thermosensitive polymer hydrogel, causing a large amount of 30% or more of the drugs to be released at an early-stage of the injection. Further, there is another problem that the release of the drug is completed in a short time due to a high rate of diffusion of a hydrophilic drug from the gel into the living body, whereby a sustained release of the drug cannot be achieved (Adv Drug Deliv Rev, 31, 197 (1998)).

Therefore, biodegradable and thermosensitive polymers in which the bioactive molecule or the drug was directly combined with a hydrogel were required. Further, because a cell is unable to grow in the gel, the thermosensitive polymer hydrogel conjugated with the bioactive molecule as the material for the implantation type cell transfer is required.

A copolymer (poloxamer) of the polyethylene oxide and polypropylene oxide is a well known thermosensitive polymer hydrogel. However, the poloxamer is not degradable in vivo [J. Pharm. Pharmacol, 48, 669 (1996)]. In a recent, a biodegradable copolymer (Regel®) of the polyethylene oxide and polylactide acid were reported [Nature, 388, 860 (1997)]. However, Regel® has the disadvantage of not having a functional group, thereby restricting the direct combination with the drugs or bioactive molecules.

The present inventors have reported that poly(organophosphazene) prepared by substitution with an amino acid ester and methoxypolyethyleneglycol in a linear dichlorophosphazene show a thermosensitivity that has a sol-phase in an aqueous solution at a specific temperature or lower, and a phase transition from the sol-phase to the gel-phase of a three-dimensional structure occurs as the temperature is raised above a specific temperature. Further, they are gradually hydrolyzed in an aqueous solution [Macromolecules 32, 2188 (1999); Macromolecules 32, 7820 (1999); Macromolecules 35, 3876 (2002); Korean Patent Nos. 259,367, and 315,630; and U.S. Pat. No. 6,319,984].

Moreover, the present inventors have developed the poly (organophosphazene)s with a functional group showing the sol-gel phase transition with change of temperature (Korean Patent application No. 2006-0005579).

A drug or bioactive molecule can be introduced to a poly (organophosphazene) with a functional group by a chemical bond such a covalent bond or coordinate covalent bond. The property of the poly(organophosphazene)s including biodistribution, biodegradation, pharmacodynamics, solubility, antigen reaction can be changed depending on the type of chemical bond.

A polymer-drug conjugate can control the emission of a drug, reduce the toxicity of a drug, and increase the medicinal effect according to the EPR effect (the effect of improved penetration and maintenance) [Bioconjugate Chem. 3, 351 (1992)]. As a representative study regarding drug delivery by such bonding, the cyclotriphosphazene-anticancer drug conjugate is known [J. Control. Release, 161, 55 (1998)].

A biodegradable and thermosensitive poly(organophosphazene) conjugated with a drug or bioactive molecule is the polymer-drug conjugate applied to the thermosensitive polymer. The poly(organophosphazene) conjugated with drug or bioactive molecule has the advantages of the polymer-drug conjugate and conventional drug carriers, so that it can effectively deliver the drug in vivo, have excellent medicinal effect, and become with the implantation type hydrogel which allows a cell to grow therein.

Moreover, the introduction of various additives to the polymer hydrogel can increase efficiency as the cell transfer material or drug. When delivering the polypeptide or the protein drug, the introduction of an additive can maintain the stability of the drug in the hydrogel, induce the ionic bonding of an additive and drugs, and control the release rate of medicine from hydrogel. Further, when delivering a treating cell, additives introduced to a hydrogel can increase the activity of a cell after being delivered into the body.

SUMMARY OF THE INVENTION

An object of the present invention is to provide poly(organophosphazene)-bioactive molecule conjugates in which poly(organophosphazene) showing the sol-gel phase transition with change of temperature is combined with various bioactive molecules, such as drugs, and a method of preparation thereof.

Another object of the present invention is to provide a hydrogel containing the poly(organophosphazene)-bioactive molecule conjugate.

Yet another object of the present invention is to provide a composition for delivery of a bioactive molecule containing the poly(organophosphazene)-bioactive molecule conjugate and/or the hydrogel and one or more selected from the group consisting of additional drugs and/or additives.

DETAILED DESCRIPTION OF THE EMBODIMENTS

Figure 1:
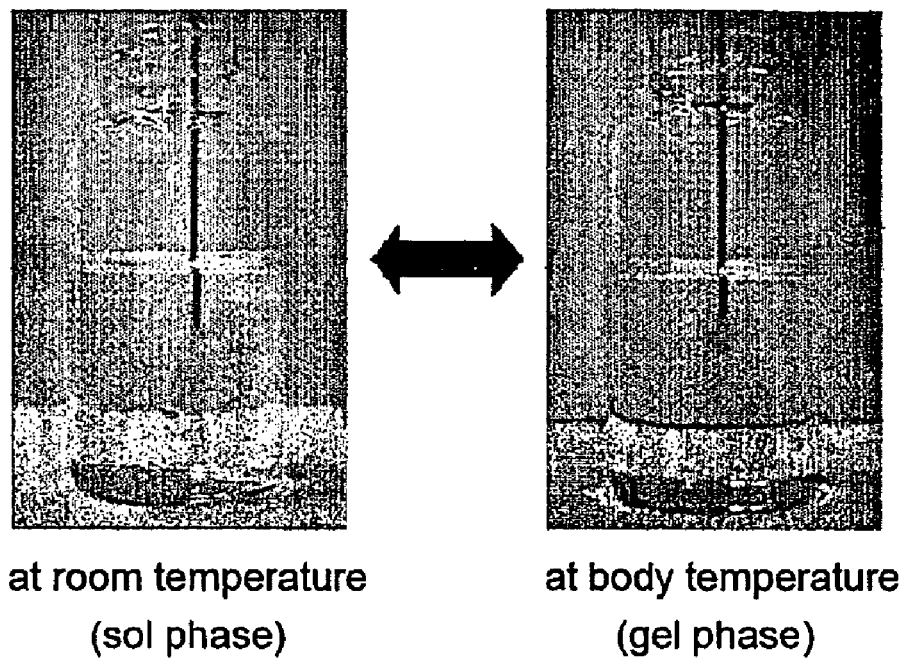
FIG. 1 is a photograph showing the sol-gel phase transition of the poly(organophosphazene) conjugated with paclitaxel of the present invention.

The present invention relates to poly(organophosphazene)-bioactive molecule conjugates in which biodegradable and thermosensitive poly(organophosphazene) having a functional group showing the sol-gel phase transition with change of temperature is combined with various bioactive molecules, such as drugs, a preparation method thereof, and a use thereof for delivery of bioactive molecules.

According to the present invention, the poly(organophosphazene) is a phosphagen-based molecule which is biodegradable and are thermosensitive and thus shows sol-gel phase transition depending on temperature change. Thus, when it is administered into a living body with bioactive molecules such as drugs, the poly(organophosphazene) forms a gel-phase at body temperature to allow the controlled release of the bioactive molecules. Further, the poly(organophosphazene) has functional groups to chemically bond with bioactive molecules through an ionic bond, covalent bond, or coordinate covalent bond to allow sustained release of the bioactive molecules due to its good binding property. Therefore, the poly(organophosphazene) is useful as a delivery material for bioactive molecules.

As used herein, the term "biodegradable" refers to a property that, when a material is injected into a living body, it breaks down in vivo into harmless substances, and is excreted out, such that it does not remain in the body, and has no harmful effect.

The term "thermosensitive" refers to the property that a material shows a sol-gel phase transition in which a solution in the sol-phase is changed into the gel-phase by raising the temperature, and the temperature where the sol-gel phase transition occurs is referred to as "gelling temperature".

The term "bioactive molecule" refers to a material which has an advantage effect in vivo. For example, the bioactive molecule is one or more selected from the group consisting of various drugs (such anti-cancer drugs and angiogenesis inhibitors), proteins, polypeptides, peptides, vaccines, genes and hormones.

In one aspect, the present invention provides poly(organophosphazene)-bioactive molecule conjugates in which poly(organophosphazene) showing the sol-gel phase transition with change of temperature is combined with one or more bioactive molecules.

The poly(organophosphazene)-bioactive molecule conjugates of the present invention may be represented by the following Chemical Formula 1:

[Chemical Formula 1]

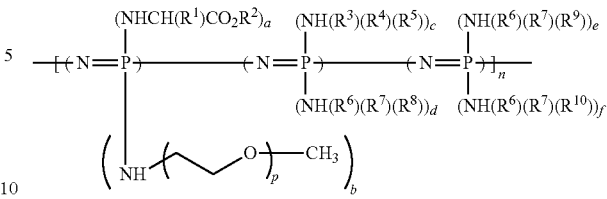

wherein, p is the number of repeating units of ethyleneglycol and is an integer between 7 and 50;

$NHCH(R^1)CO_2R^2$ is an amino acid ester, wherein $R^1$ is selected from the group consisting of H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2H_2C_6H_4$, $OCOC_4N^+H_9$, $CO_2C_2H_5$, $CH_2CO_2C_2H_5$, $(CH_2)_2CO_2C_2H_5$, and $HCONHCH(CH_2C_6H_5)$, and $R^2$ is selected from the group consisting of $CH_3$, $C_3H_7$, $C_4H_9$, $C_2H_5$, $CH_2C_6H_5$, and $CH_2CHCH_2$;

$NH(R^3)(R^4)(R^5)$ is an amino acid, peptide, or depsipeptide ester, wherein $R^3$ is $CH(W)$, $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is $CH(Y)$, $R^7$ is selected from the group consisting of $C_2H_4$, $C_3H_6$, $C_4H_8$, $CH_2C_6H_4$, $CH_2CO_2$, O, $CONHCH(Z)O$, CO, $CO_2$, S, $CONHCH(Z)S$, N, $CONHCH(Z)N$, CON, $COCHNH(Z)$ CON, $CONHCH(Z)CO$, and $CONHCH(Z)CO_2$, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups as shown in the following Table 1, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamines, q is the number of repeating units of methylene and is an integer between 1 and 20, r is the number of repeating units of ethyleneimine, lysine, or arginine and is an integer between 1 and 18000;

$NH(R^6)(R^7)(R^{10})$ is substituents having a functional group, wherein $R^6$ and $R^7$ is the same in $NH(R^6)(R^7)(R^8)$ and $NH(R^6)(R^7)(R^9)$, $R^{10}$ is selected from the group consisting of paclitaxel, doxorubicin, camptothecin, epirubicine, 5-fluorouracil, 10-hydroxycamptothecin, 10-aminocamptothecin, 7-ethyl-camptothecin, irinotecan, methotrexate, mitomycin C, taxoid, docetaxel, chlorambucil, calicheamicin, maytansinoid, 2-pyrrolino-doxorubicin (AN-201), daunorubicin, butyric acid, melphalan, 4'-dimethyldeoxypodophyllotoxin, curcumin, podophyllotoxin, epipodophyllotoxin, 4-β-amino-4'-O-demethylepipodophyllotoxin, tallysomycin $S_{10b}$, daunomycin, duocarmycin A, duocarmycin SA, cis-aconityl-daunomycin, calicheamicin, diazeniumdiolate, netropsin, 6-metcaptopurine, glucuronidation, phosmidosine, streptonigrin, hematoporphyrin, desferrioxamine (DFO), deferiprone, acivicin, estramustine, enediyne, arginine-glycin-aspatic acid peptide, neuropeptides (such as neurotensin, tachykinin, neuropeptide Y (NPY), peptide YY (PYY), vasoactive intestinal polypeptide (VIP), and pituitray adenylate cyclase-activating polypeptide (PACAP)), albumin, Bovin serum albumin (BSA), bovin pancreatic ribonuclease (RNase A), Bovin seminal ribonuclease (BS-RNase), Bowman-birk protease inhibitor (BBI), collagen, fibronetin, laminin, erythropoietin (EPO), interferon, hirudin, colony stimulating factor (CSF), insulin, desmopressin, glucagon-like peptide 1 (GLP1), human growth hormone antagonist, tumor necrosis factor receptor 1 (TNFR1), asparaginase, adenosine deaminase, bone morphogenetic proteins (BMPs), growth factors (such as fibroblast growth factor (FGF), vascular endothelial growth factor (VEGF), epidermal growth factor (EGF), nerve growth factor (NGF), platelet derived growth factor (PDFG), insulin like growth factor (IGF), transforming growth factor-beta (TGF-β), brain-derived neurotrophic factor (BDNF), neurotrophin-2 (NT-3) and neurotrophin-4/5 (NT-4/5)), tumor necrosis factor-related apoptosis-inducing ligand (TRAIL), cytokines [such as interferon-alpha 1a (IFN-α 1a), interferon-alpha 2a (IFN-α 2a), interferon-alpha 2b (IFN-α 2b), interferon-gamma (IFN-γ), interleukin-1 (IL-1), interleukin-2 (IL-2), interleukin-3 (IL-3), interleukin-4 (IL-4), interleukin-5 (IL-5) and interleukin-6 (IL-6), tumor necrosis factor-alpha (TNF-α) and leukemia-inhibitory factor (LIF)], theanine dexamethason, heparin, chitosan, hyaluronan, cyclodextran, starch, carbohydrate, saccharide, fluorescent protein (such as green fluorescent protein (GFP) and red fluorescent protein (RFP)), virus-like particle (VLP), and vaccine, a, b, c, d, e, and f respectively represent the content of each substituent, wherein a, b, and f are independently from 0.01 to 1.9, c, d, and e are independently from 0 to 1.9, and a+b+c+d+e+f=2.0; and n is the degree of polymerization of the poly(organophosphazene) and is from 5 to 100000.

The protamine used as $R^9$ is not limited in the molecular weight, but preferably has a molecular weight from 4,000 to 10,000.

The available protecting groups are summarized in the following Table 1, but not limited thereto:

TABLE 1

| Functional group | Protecting group (R'=$R^5$) |
|---|---|
| Carboxyl group (RCOOR') | Fluorenylmethyl ester, Methoxymethyl ester($CH_2OCH_3$), Methylthiomethyl ester($CH_2SCH_3$), Tetrahydrofuranyl ester, Methoxyethoxymethyl ester($CH_2OCH_2CH_2OCH_3$), 2-(trimethylsilyl)ethoxymethyl ester($CH_2OCH_2CH_2Si(CH_3)_3$), Benzyloxymethyl ester($CH_2OCH_2C_6H_5$), Pivaloxyloxymethyl ester($CH_2O_2CC(CH_3)_3$), Phenylacetoxymethyl ester($CH_2O_2CCH_2Ph$), Triisopropylsilylmethyl ester($CH_2Si$-i-$Pr_3$), Cyanomethyl ester($CH_2CN$), Acetol ester($CH_2COCH_3$), Phenacyl ester($CH_2COC_6H_5$), p-Bromophenacyl ester($CH_2COC_6H_4$-p-Br), α-Methylphenacyl ester($CH(CH_3)COC_6H_5$). p-Methoxyphenacyl ester($CH_2COC_6H_4$-p-$OCH_3$), Desyl ester, Carboxamidomethyl ester($CH_2CONH_2$), p-Azobenzenecaeboxamidomethyl ester($CH_2(O)CNHC_6H_4N=NC_6H_5$), N-Phthalimidomethyl ester, 2,2,2-Trichloroethyl ester($CH_2CCl_3$), 2-Haloethyl ester($CH_2CH_2X$, X=I, Br, Cl), ω-Chloroalkyl ester($(CH_2)_nCl$, n = 4, 5), 2-(trimethylsilyl)ethyl ester($CH_2CH_2Si(CH_3)_3$), 2-Methylthioethyl ester($CH_2CH_2SCH_3$), 1,3-Dithianyl-2-methyl ester, 2-(p-Nitrophenylsulfenyl)ethyl ester($CH_2CH_2SC_6H_4$-p-$NO_2$), 2-(p-Toluenesulfonyl)ethyl ester($CH_2CH_2SO_2C_6H_4$-p-$CH_3$), 2-(2'-Pyridyl)ethyl ester($CH_2CH_2$-2-$C_5H_4N$), 2-(p-Methoxyphenyl)ethyl ester($CH_2CH_2C_6H_4O$-p-$CH_3$), 2-(diphenylphosphino)ethyl ester($CH_2CH_2P(C_6H_5)_2$), 1-Methyl-1-phenylethyl ester($C(CH_3)_2C_6H_5$), 2-(4-Acetyl-2-nitrophenyl)ethyl ester, 2-Cyanoethyl ester($CH_2CH_2CHN$), t-Butyl ester($C(CH_3)_3$), 3-Methyl-3-pentyl ester($CCH_3(C_2H_4)_2$), Dicyclopropylmethyl ester, 2,4-Dimethyl-3-pentyl ester($CH(i-Pr)_2$), Cyclopentyl ester(c-$C_5H_9$), Cyclohexyl ester(c-$C_6H_{11}$), Allyl ester($CH_2CH=CH_2$), Methallyl ester($CH_2(CH_3)C=CH_2$), 2-Methylbut-3-en-2-yl ester($C(CH_3)_2CH=CH_2$), 3-Methylbut-2-enyl ester($CH_2CH=C(CH_3)_2$), 3-Buten-1-yl ester($CH_2CH_2CH=CH_2$), 4-(Trimethylsilyl)-2-buten-1-yl ester($CH_2CH=CHCH_2Si(CH_3)_3$), Cinnamyl ester($CH_2CH=CHC_6H_5$), α-Methylcinnamyl ester($CH(CH_3)CH=CHC_6H_5$), Prop-2-ynyl ester($CH_2C=CH$), Phenyl ester($C_6H_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester($C_6H_4$-p-$SCH_3$), Pentafluorophenyl ester($C_6F_5$), Benzyl ester($CH_2C_6H_5$), Triphenylmethyl ester($C(C_6H_5)_3$), Diphenylmethyl ester($CH(C_6H_5)_2$) Bis(o-nitrophenyl)methyl ester($CH(C_6H_4$-o-$NO_2)_2$), 9-Anthrylmethyl ester($CH_2$-9-Anthryl), 2-(9,10-Dioxo)anthrylmethyl) ester, 5-dibenzosuberyl ester, 1-Pyrenylmethyl ester, 2-(trifluoromthyl)-6-chromonylmethyl ester, 2,4,6-Trimethylbenzyl ester($CH_2C_6H_2$-2,4,6-$(CH_3)_3$), p-Bromobenzyl ester($CH_2C_6H_4$-p-Br), o-Notrobenzyl ester($CH_2C_6H_4$-o-$NO_2$), p-Nitrobenzyl ester($CH_2C_6H_4$-p-$NO_2$), p-Methoxybenzyl ester($CH_2C_6H_4$-p-$OCH_3$), 2,6-Dimethoxybenzyl ester($CH_2C_6H_3$-2,6-$(OCH_3)_2$, 4-(Methylsulfinyl)benzyl ester($CH_2C_6H_4(O)S$-4-$CH_3$), 4-Sulfobenzyl ester($CH_2C_6H_4SO_3^-Na^+$), 4-Azidomethoxybenzyl ester($CH_2C_6H_4OCH_2N_3$), 4-{N-[1-(4,4-Dimethyl-2,6-dioxocyclohexylidene)-3-methlbutyl]amino}benzyl ester, Piperonyl ester, 4-Picolyl ester($CH_2$-4-pyridyl), p-P-Benzayl ester($CH_2C_6H_4$-p-P), Trimethtylsilyl ester($Si(CH_3)_3$), Triethylsilyl ester($Si(C_2H_5)_3$), t-Butyldimethylsilyl ester($Si(CH_3)_2C(CH_3)$, i- |

TABLE 1-continued

| Functional group | Protecting group (R'=R$^5$) |
|---|---|
| Thiol group (RSR') | Propyldimethylsilyl ester(Si(CH$_3$)$_2$CH(CH$_3$)$_2$), Phenyldimethylsilyl ester(Si(CH3)$_2$C$_6$H$_5$), Di-t-butylmethylsilyl ester(SiCH$_3$(t-Bu)$_2$), Triisopropylsilyl ester S-Alkyl thioether(C$_n$H$_{2n+1}$), S-Benzyl thioether(CH$_2$Ph), S-p-Methoxylbenzyl thioether(CH$_2$C$_6$H$_4$-p-OCH$_3$), S-o- or p-Hydroxy-or-Acetoxybenzyl thioether(CH$_2$C$_6$H$_4$-o-(or p-)-OR', R'=H or Ac), S-p-Nitrobenzyl thioether(CH$_2$C$_6$H$_4$-p-NO$_2$), S-2,4,6-Trimethylbenzyl thioether(CH$_2$C$_6$H$_2$-2,4,6-Me$_3$), S-2,4,6-Trimethoxybenzyl thioether(CH$_2$C$_6$H$_2$-2,4,6-(OMe)$_3$), S-4-Picolyl thioether(CH$_2$-4-pyridyl), S-2-Quinolinylmethyl thioether, S-2-Picolyl N-Oxide thioether(CH$_2$-2-pyridyl N-Oxide), S-9-Anthrylmethyl thioether(CH$_2$-9-anthtyl), S-9-Fluorenylmethyl thioether, S-Xanthenyl thioether, S-Ferrocenylmethyl thioether, S-Diphenylmethyl thioether(CH(C$_6$H$_5$)$_2$), S-Bis(4-methoxyphenyl)methyl thioether(CH(C$_6$H$_4$-4-OCH$_3$)$_2$), S-Bis(4-methoxyphenyl)phenylmethyl thioether, S-5-Dibenzosuberyl thioether, S-Triphenylmethyl thioether(C(C$_6$H$_5$)$_3$), S-Diphenyl-4-pyridylmethyl thioether(C(C$_6$H$_5$)$_2$-4-pyridyl), S-Phenyl thioether(C$_6$H$_5$), S-2,4-Dinitrophenyl thioether(C$_6$H$_3$-2,4-(NO$_2$)$_2$), S-t-Butyl thioether(C(CH$_3$)$_3$), S-1-Adamantyl thioether, S-Methoxymethyl monothioacetal(CH$_2$OCH$_3$), S-Isobutoxymethyl monothioacetal(CH$_2$OCH$_2$CH(CH$_3$)$_2$), S-Benzyloxymethyl monothioacetal(CH$_2$OBn), S-2-Tetrahhydropyranyl monothioacetal, S-Benzylthiomethyl dithioacetal(CH$_2$SC$_6$H$_5$), S-Phenylthiomethyl dithioacetal(CH$_2$SC$_6$H$_5$), S-Acetamidometyl thioacetal(CH$_2$NHCOCH$_3$), S-Trimethylacetamidomethyl thioacetal(CH$_2$NHCOC(CH$_3$)$_3$), S-Benzamidomethyl(thioacetalCH$_2$NHCOC$_6$H$_5$), S-Allyloxycarbonylaminomethyl thioacetal(CH$_2$NH(O)COCH$_2$CH=CH$_2$), S-Phenylacetamidomethyl thioacetal(CH$_2$NH(O)CCH$_2$C$_6$H$_5$), S-Phthalimidomethyl thioacetal, S-Acetyl-, S-Carboxy, and S-Cyanomethyl thioether(CH$_2$X, X = —COCH$_3$, —CO$_2$H, —CN), S-(2-Nitro-1-phenyl)ethyl thioether(CH(C$_6$H$_5$)CH$_2$NO$_2$), S-2-(2,4-Dinitrophenyl)ethyl thioether, S-2-(4'-Pyridyl)ethyl thioether(CH$_2$CH$_2$NC$_4$H$_4$), S-2-Cyanoethyl thioether(CH$_2$CH$_2$CN), S-2-(Trimethylsilyl)ethyl thioether(CH$_2$CH$_2$TMS), S-2,2-Bis(carboethoxy)ethyl thioether(CH$_2$CH(COOC$_2$H$_5$)$_2$), S-(1-m-Nitrophenyl-2-benzoyl)ethyl thioether(CH(C$_6$H$_4$-m-NO$_2$)CH$_2$COC$_6$H$_5$), S-2-phenylsulfonylethyl thioether(CH$_2$CH$_2$SO$_2$Ph), S-1-(4-Methylphenylsulfonyl)-2-methylprop-2-yl thioether(C(CH$_3$)$_2$CH$_2$SO$_2$C$_6$H$_4$-4-CH$_3$), Triisopropylsilyl thioether, S-Acetyl derivative(COCH$_3$), S-Benzoyl derivative(COC$_6$H$_5$), S-Trifluoroacetyl derivatives(COCF$_3$), S-2,2,2-Trichloroethoxycarbonyl derivatives(COOCH$_2$CCl$_3$), S-t-Butoxycarbonyl derivatives(COOC(CH$_3$)$_3$), S-Benzyloxycarbonyl derivatives(COOCH$_2$C$_6$H$_5$), S-p-Methoxybenzyloxycarbonyl derivatives(COOCH$_2$C$_6$H$_4$-p-OCH$_3$), S—(N-Ethylcarbamate)(CONHC$_2$H$_5$), S—(N-Methoxymethylcarbamate)(CONHCH$_2$OCH$_3$), S-Ethyl disulfide(SC$_2$H$_5$), S-t-Butyl disulfide(SC(CH$_3$)$_3$) |
| Hydroxy group (ROR') | Methyl ether(CH$_3$), Methoxymethyl ether(CH$_2$OCH$_3$), Methylthiomethyl ether(CH$_2$SCH$_3$), (Phenyldimethylsilyl)methoxymethyl ether(CH$_2$OCH$_2$Si(CH$_3$)$_2$C$_6$H$_5$), Benzyloxymethyl ether(CH$_2$OCH$_2$Ph), p-Methoxybenzyloxymethyl ether(CH$_2$OCH$_2$C$_6$H$_4$O-p-Me), p-Nitrobenzyloxymethyl ether(CH$_2$OCH$_2$C$_6$H$_4$-4-NO$_2$), o-Nitrobenzyloxymethyl ether(CH$_2$OCH$_2$C$_6$H$_4$-2-NO$_2$), (4-Methoxyphenoxy)methyl ether(CH$_2$OC$_6$H$_4$-4-OCH$_3$), Guaiacolmethyl ether(CH$_2$OC$_6$H$_4$-2-OMe), t-Butoxymethyl ether(CH$_2$O-t-Bu), 4-Pentenyloxymethyl ether(CH$_2$OCH$_2$CH$_2$CH=CH$_2$), Siloxymethyl ether(CH$_2$OSiR'R'', R' = t-Bu, R'' = Me; R' = Thexyl, R'' = Me; R' = t-Bu, R'' = Ph), 2-Methoxyethoxymethyl ether(CH$_2$OCH$_2$CH$_2$OCH$_3$), 2,2,2-Trichloroethoxymethyl ether(CH$_2$OCH$_2$CCl$_3$), Bis(2-chloroethoxy)methyl ether(CH(OCH$_2$CH$_2$Cl)$_2$), 2-(Trimethylsilyl)ethoxymethyl ether(CH$_2$OCH$_2$CH$_2$SiMe$_3$), Memthoxymethyl ether, Tetrahydropyranyl ether, 3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, Tetrahydrothiofuranyl ether, 2,3,3a,4,5,6,7,7a-octahydro-7,8,8-trimethyl-4,7-methanobenzofuran-2-yl ether, 1-Ethoxyethyl ether(CH(OC$_2$H$_5$)CH$_3$), 1-(2-Chloroethoxy)ethyl ether(CH(CH$_3$)OCH$_2$CH$_2$Cl), 1-[2-(Trimethylsilyl)ethoxy]ethyl ether, 1-Methyl-1-methoxyethyl ether(C(OCH$_3$)(CH$_3$)$_2$), 1-Methyl-1-benzyloxyethyl ether(C(OBn)(CH$_3$)$_2$), 1-Methyl-1-benzyloxy-2-fluoroethyl ether(C(OBn)(CH$_2$F)(CH$_3$), 1-Methyl-1-phenoxyethyl ether(C(OPh)(CH$_3$)$_2$), 2,2,2-trichloroethyl ether(CH$_2$CCl$_3$), 1,1-Dianisyl-2,2,2-trichloroethyl ether,1,1,1,3,3,3-Hexafluoro-2-phenylisopropyl ether(C(CHF$_3$)$_2$Ph), 2-Trimethylsilylethyl ether(CH$_2$SiMe$_3$), 2-(Benzylthio)ethyl ether(CH$_2$CH$_2$SBn), 2-(Phenylselenyl)ethyl ether(CH$_2$CH$_2$SePh), t-Butyl ether, Allyl ether(CH$_2$CH=CH$_2$), Propargyl ether(CH$_2$C≡CH), p-Methoxyphenyl ether(C$_6$H$_4$O-p-Me), p-Nitrophenyl ether(C$_6$H$_4$-p-NO$_2$), 2,4-Dinitrophenyl ether(C$_6$H$_3$-2,4-(NO$_2$)$_2$), 2,3,5,6-Tetrafluoro-4-(trifluoromethyl)phenyl ether(C$_6$F$_4$CF$_3$), Benzyl ether(CH$_2$Ph), p-Methoxybenzyl ether(CH$_2$C$_6$H$_4$-p-OMe), 3,4-Dimethoxybenzyl ether(CH$_2$C$_6$H$_3$-3,4-(OMe)$_2$), o-Nitrobenzyl ether(CH$_2$C$_6$H$_4$-o-NO$_2$), p-Nitrobenzyl ether(CH$_2$C$_6$H$_4$-p-NO$_2$), p-Halobenzyl ether(CH$_2$C$_6$H$_4$-p-X, X=Br, Cl), 2,6-Dichlorobenzyl ether(CH$_2$C$_6$H$_3$-2,6-Cl$_2$), p-Cyanobenzyl ether(CH$_2$C$_6$H$_4$-p-CN), p-Phenylbenzyl ether(CH$_2$C$_6$H$_4$-p-C$_6$H$_5$), 2,6-Difluorobenzyl ether(CH$_2$C$_6$H$_3$F$_2$), p-Acylaminobenzyl ether(CH$_2$C$_6$H$_3$-p-NHCOR'), p-Azidobenzyl ether(CH$_2$C$_6$H$_4$-4-N$_3$), 4-Azido-3-chlorobenxyl ether(CH$_2$C$_6$H$_3$-3-Cl-4-N$_3$), 2-Trifluoromethylbenzyl ether(CH$_2$C$_6$H$_4$-2-CF$_3$), p-(Methylsulfinyl)benzyl ether(CH$_2$C$_6$H$_4$-p-(MeS(O)), 2- and 4-Picolyl ether(CH$_2$C$_5$H$_4$N), 3-Methyl-2-picolyl N-Oxide ether, 2-Quinolinylmethyl ether, 1-Pyrenylmethyl ether, Diphenylmethyl ether(CHPh$_2$), p,p'-Dinitrobenzhydryl ether(CH(C$_6$H$_4$-p-NO$_2$)$_2$), 5-Dibenzosuberyl ether, Triphenylmethyl ether, p-Methoxyphenyldiphenylmethyl ether(C(Ph)$_2$C$_6$H$_4$-p-OMe), Di(p-methoxyphenyl)phenylnethyl ether(CPh(p-MeOC$_6$H$_4$)$_2$), Tri(p- |

TABLE 1-continued

| Functional group | Protecting group (R'=R$^5$) |
|---|---|
| | methoxyphenyl)methyl ether(C(p-MeOC$_6$H$_4$)$_3$), 4-(4'-Bromophenacyloxy)phenyldiphenylmethyl ether(C(Ph)$_2$C$_6$H$_4$-p-(OCH$_2$(O)CC$_6$H$_4$-p-Br), 4,4',4''-Tris(4,5-dichlorophthalimidophenyl)methyl ether, 4,4',4''-Tris(levulinoyloxyphenyl)methyl) ether, 4,4'4''-Tris(benzoyloxyphenyl)methyl) ether, 4,4'-Dimethoxy-3''-[N-(imidazolylmethyl)]trityl ether, 4,4'-Dimethoxy,3''-[N-(imidazolylethyl)carbamoyl)trityl ether, 1,1-Bis(4-methoxyphenyl)-1-pytenylmethyl ether, 4-(17-tetrabenzo[a,c,g,i]fluorenylmethyl)-4',4''-dimethoxytrityl ether, 9-Anthryl ether, 9-(9-Phenyl)xanthenyl ether, Tritylone ether, 1,3-Benzodithiolan-2-yl ether, Benzisothiazolyl-S,S-dioxido ether, Trimethylsilyl(Si(CH$_3$)$_3$) ether, Triethylsilyl(SiEt$_3$) ether, Triisopropylsilyl(Si(i-Pr)$_3$) ether, Dimethylisopropylsilyl(SiMe$_2$-i-Pr) ether, Diethylisopropylsilyl(SiEt$_2$-i-Pr) ether, Dimethylthesilyl ether((CH$_3$)$_2$Si(CH$_3$)$_2$CCH(CH$_3$)$_2$), t-Butyldimethylsilyl ether(SiMe$_2$-t-Bu), t-Butyldiphenylsilyl ether(SiPh$_2$-t-Bu), Tribenxylsily ether(Si(CH$_2$C$_6$H$_5$)$_3$), Tri-p-xylylsilyl ether(Si(CH$_2$C$_6$H$_4$-p-CH$_3$)$_3$), Triphenylsilyl ether(SiPh$_3$), Diphenylmethylsily ether(SiMePh$_2$), Di-t-butylmethylsilyl ether(SiMe(t-Bu)$_2$),Tris(trimethylsilyl)silyl ether([Si[Si(CH$_3$)$_3$]$_3$), (2-Hydroxystyryl)dimethylsilyl ether, (2-Hydroxystyryl)diisopropulsilyl ether, t-Butylmethoxyphenylsilyl ether(SiPh(OCH$_3$)-t-Bu), t-Butoxydiphenylsilyl ether(Si(t-OBu)Ph$_2$), Formate ester(CHO), Benzoylformate ester(COCOPh), Acetate ester(COCH$_3$), Chloroacetate ester(COCH$_2$Cl), Dichloroacetate ester(COCHCl$_2$), Trichloroacetate ester(COCCl$_3$), Trifluoroacetate ester(COCF$_3$), Methoxyacetate ester(COCH$_2$OMe), Triphenylmethoxyacetate ester(COCH$_2$OCPh$_3$), Phenoxyaetate ester(COCH$_2$OPh), p-chlorophenoxyacetate ester(COCH$_2$OC$_6$H$_4$-p-Cl), phenylacetate ester(COCH$_2$Ph), p-P-Phenylacetate ester(COCH$_2$C$_6$H$_4$-p-P), Diphenylacetate ester(COCHPh$_2$), Nicotinate ester, 3-Phenylpropionate ester(COCH$_2$CH$_2$Ph), 4-Pentenoate ester(COCH$_2$CH$_2$CH=CH$_2$), 4-Oxopentanoate ester(COCH$_2$CH$_2$COCH$_3$), 4,4-(Ethylenedithio)pentanoate ester, 5-[3-Bis(4-methoxyphenyl)hydroxymethylphenoxy]levulinic acid ester, Pivaloate(COC(CH$_3$)$_3$) ester, Crotonate ester(COCH=CHCH$_3$), 4-Methoxycrotonate ester(COCH=CHCH$_2$OCH$_3$), Benzoate ester(COPh), p-Phenylbenzoate ester(COC$_6$H$_4$-p-C$_6$H$_5$), 2,4,6-Trimethylbenzoate ester(COC$_6$H$_2$-2,4,6-Me$_3$), Alkyl methyl carbonate(CO$_2$CH$_3$), Methoxymethyl carbonate(CO$_2$CH$_2$OCH$_3$), alkyl 9-fluorenylmetyl carbonate, Alkyl ethyl carbonate(CO$_2$Et), Alkyl 2,2,2-Trichloroethyl carbonate(CO$_2$CH$_2$CCl$_3$), 1,1-Dimethyl-2,2,2-trichloroethyl carbonate(CO$_2$C(CH$_3$)$_2$CCl$_3$), Alkyl 2-(trimethylsilyl)ethyl carbonate(CO$_2$CH$_2$CH$_2$SiMe$_3$), Alkyl 2-(phenylsulfonyl)ethyl caronate(CO$_2$CH$_2$CH$_2$SO$_2$Ph), Alkyl isobutyl carbonate(CO$_2$CH$_2$CH(CH$_3$)$_2$), Alkyl vinyl carbonate(CO$_2$CH=CH$_2$), Alkyl allyl carbonate(CO$_2$CH$_2$CH=CH$_2$), Alkyl p-nitrophenyl carbonate(CO$_2$C$_6$H$_4$-p-NO$_2$), Alkyl benzyl carbonate(CO$_2$Bn), Alkyl p-methoxybenzyl carbonate(CO$_2$C$_6$H$_4$-p-OMe), Alkyl 3,4-dimethoxybenzyl carbonate(CO$_2$CH$_2$C$_6$H$_3$-3,4-(OMe)$_2$), Alkyl o-nitrobenzyl carbonate(CO$_2$CH$_2$C$_6$H$_4$-o-NO$_2$), Alkyl p-nitrobenzyl carbonate(CO$_2$CH$_2$C$_6$H$_4$-p-NO$_2$), 2-Dansylethyl carbonate, 2-(4-Nitrophenyl)ethyl carbonate(CO$_2$CH$_2$CH$_2$C$_6$H$_4$-4-NO$_2$), 2-(2,4-dinitrophenyl)ethyl carbonate(CO$_2$CH$_2$CH$_2$C$_6$H$_3$-2,4-(NO$_2$)$_2$), 2-Cyano-1-phenylethyl carbonate(CO$_2$(C$_6$H$_5$)CHCH$_2$CN), Alkyl S-Benzyl thiocarbonate(COSCH$_2$Ph), Alkyl 4-ethoxy-1-naphthyl carbonate, Alkyl methyl dithiocarbonate(SCSCH$_3$), 2-iodobenzoate ester(COC$_6$H$_4$-2-I), 4-Azidobutyrate ester(CO(CH$_2$)$_3$N$_3$), 4-Nitro-4-methylpentanoate ester, o-(dibromomethyl)benzoate ester(COC$_6$H$_4$-o-(CHBr$_2$)), 2-Formylbenzenesulfonate ester, Alkyl 2-(methylthiomethoxy)ethyl carbonate(CO$_2$CH$_2$CH$_2$OCH$_2$SCH$_3$), 4-(Methylthiomethoxy)butyrate ester(CO(CH$_2$)$_3$OCH$_2$SCH$_3$), 2-(Methylthiomethoxymethyl)benzoate ester(COC$_6$H$_4$-2-(CH$_2$OCH$_2$SCH$_3$)), 2-(Chloroacetoxymethyl)benzioate ester, 2-[(2-chloroacetoxy)ethyl]benzoate ester, 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester), p-P-Benzoate ester, α-Naphthoate ester, Nitrate ester, Alkyl N,N,N',N'-tetramethylphosphorodiamidate, 2-Chlorobenzoate ester, 4-Bromobenzoate ester, 4-Nitrobenzoate ester, 3,5-Dimethoxybenzoin carbonate, A wild and woolly photolabiled fluorescent ester, Alkyl N-phenylcarbamate, Borate ester, Dimethylphosphinothioyl ester((S)P(CH$_3$)$_2$), Alkyl 2,4-dinitrophenylsulfenate(SC$_6$H$_3$-2,4-(NO$_2$)$_2$), Sulfate, Allylsulfonate(SOCH$_2$CH=CH$_2$), Methanesulfonate (SO$_2$Me), Benzylsulfonate(SO$_2$Bn), Tosylate(SO$_2$C$_6$H$_4$CH$_3$),2-[(4-Nitrophenyl)ethyl]sulfonate(SO$_2$CH$_2$CH$_2$C$_6$H$_4$-4-NO$_2$) |
| Amino group (RNR') | Fromamide(CHO), Acetamide(Ac), Chloroacetamide(COCH$_2$Cl), Trichloroacetamide(COCCl$_3$), Trifluoroacetamide(COCF$_3$), Phenylacetamide(COCH$_2$C$_6$H$_5$), 3-Phenylpropanamide(COCH$_2$CH$_2$C$_6$H$_5$), Pent-4-enamide((O)CH$_2$CH$_2$CH=CH$_2$), Picolinamide(CO-2-pyridyl), 3-Pyridylcarboxamide(CO-3-Pyridyl), N-Benzoylphenylalanyl derivatives(COCH(NHCOC$_6$H$_5$)CH$_2$C$_6$H$_5$), Benzamide(COC$_6$H$_5$), p-Phenybenzamide(COC$_6$H$_4$-p-C$_6$H$_5$) |
| Amide group (CORNR') | N-Allylamide(CH$_2$CH=CH$_2$), N-t-Butylamide(t-Bu), N-Dicyclopropylmethylamide(CH(C$_3$H$_5$)$_2$), N-Methoxymethylamide(CH$_2$OCH$_3$), N-Methylthiomethylamide(CH$_2$SCH$_3$), N-Benzyloxymethylamide(CH$_2$OCH$_2$C$_6$H$_5$), N-2,2,2-Trichloroethoxymethylamide(CH$_2$OCH$_2$CCl$_3$), N-t-Butyldimethylsiloxymethylamide(CH$_2$OSi(CH3)$_2$-y-C$_4$H$_9$), N-Pivaloyloxymethylamide(CH$_2$CO$_2$C(CH$_3$)$_3$), N-Cyanomethylamide(CH$_2$CHN), N-Pyrrolidinomethylamide, N-Methoxyamide(OMe), N-Benzyloxyamide(OCH$_2$C$_6$H$_5$), N- |

TABLE 1-continued

| Functional group | Protecting group (R'=R⁵) |
|---|---|
| | Methylthioamide(SMe), N-Triphenylmethylthioamide(SCPh₃), N-t-Butyldiethylsilylamide(Si(CH₃)₂-t-C₄H₉), N-Triisopropylsilylamide(Si(i-Pr)₃), N-4-Methoxyphenylamide(C₆H₄-4-OCH₃), N-4-(Methoxymethoxy)phenylamide(C₆H₄(OCH₃)₂), N-2-Methoxy-1-naphthylamide(C₁₀H₆-2-OCH₃), N-Benzylamide(CH₂C₆H₅), N-4-Methoxybenzylamide(CH₂C₆H₄-4-OCH₃), N-2,4-Dimethoxybenzylamide N-3,4-Dimethoxybenzylamide(CH₂C₆HH₃-2,4(3,4)-(OCH₃)₂), N-2-Acetoxy-4-methoxybenzylamide(CH₂C₆HH₃-4-OMe-2-Ac), N-o-nitrobenzylamide(CH₂C₆H₄-2-NO₂), N-Bis(4-methoxyphenyl)methylamide(CH(C₆H₄-4-OMe)₂), N-Bis(4-(methoxyphenyl)phenylmethylamide(CPh-(C₆H₄-4-OMe)₂), N-Bis(4-methylsulfinylphenyl)methylamide(CH(C₆H₄(O)S-4-Me)₂), N-Triphenylmethylamide(C(C₆H₅)₃), N-9-Phenylfluorenylamide, N-t-Butoxycarbonylamide(CO-t-OC₄H₉), N-benzyloxycarbonylamide, N-Methoxycarbonylamide(COOMe), N-Ethoxycarbonylamide(COOEt), N-p-Toluenesulfonylamide, N-Butenylamide(CH=CHCH₂CH₃), N-[(E)-2-(Methoxycarbonyl)vinyl]amide(CH=CCO₂Me), N-Diethoxymethylamide(CH(OEt)₂), N-(1-Methoxy-2,2-dimethylpropyl)amide, N-2-(4-Methylphenylsulfonyl)ethylamide(CH₂CH₂SO₂C₆H₄-4-CH₃) |

In one embodiment of the poly(organophosphazene)s of the present invention, a hydrophobic amino acid ester and hydrophilic methoxy-polyethyleneglycol having the molecular weight of 350 to 2,500 are introduced into the linear polymer of dichloro phosphazene so that the polymer can show thermosensitivity and biodegradability. Further, amino acid, peptide, and depsipeptide ester capable of controlling the degradation rate of the polymer may be partially introduced into the polymer.

In another embodiment of the present invention, the functional groups may be introduced into the poly(organophosphazene) using various methods, e.g., by directly introducing a substituent with functional groups such as hydroxyl, amide, amino, thiol, or carboxyl group on the side chain into the main chain, or introducing the amino acid ester or peptide ester substituted, wherein said functional group is protected with a blocking group into the main chain of the polymer followed by removing the blocking group.

In another embodiment of the present invention, lysine, arginine, cystein, thiol alkylamine, polyethyleneimines, polylysines, polyarginines, or protamines with various molecular weights may be reacted with the poly(organophosphazene) with carboxylic acid, to be introduced into the polymer as a functional group.

The gelling temperature where the sol-gel phase transition occurs, gel solidity, and/or biodegradation rate of the poly(organophosphazene) of the present invention may be controlled by the kind of hydrophobic amino acid ester, the kind of amino acid, peptide, or depsipeptide capable of controlling the degradation rate, the kind of substituent with the functional group, the chain length of methoxy polyethyleneglycol, the composition of all substituents, the molecular weight of the poly(organophosphazene), the polydispersity index, the concentration of the poly(organophosphazene) solution, and the like.

For example, as the content of the hydrophobic amino acid increases, the gelling temperature becomes lower. As the concentration of the poly(organophosphazene) solution increases, the gelling temperature becomes lower and the gel solidity increases. As the chain length of methoxy polyethylene glycol increases, the gelling temperature becomes higher and the gel solidity increase. The poly(organophosphazene) with depsipeptide ester shows a higher biodegradation rate compared with a poly(organophosphazene) without depsipeptide ester. The poly(organophosphazene) with a carboxylic acid functional group shows a higher biodegradation rate compared with a poly(organophosphazene) without the carboxylic acid functional group.

In another aspect, the present invention provides a method for preparing the poly(organophosphazene)-bioactive molecule conjugates in which poly(organophosphazene) showing the sol-gel phase transition with change of temperature is combined with a bioactive molecule, as represented by Chemical Formula 1.

The preparation method of the present invention may include the following steps of:

(1) thermopolymerizing a phosphazene trimer represented by the following Chemical Formula 2, to prepare a linear polymer of dichloro phosphazene represented by the following Chemical Formula 3

[Chemical Formula 2]

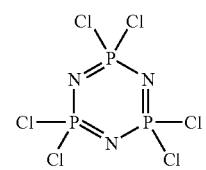

[Chemical Formula 3]

$$-\!\!+\!\!N\!\!=\!\!\overset{\underset{|}{Cl}}{\underset{Cl}{P}}\!\!\!+_n\!\!-$$

(wherein n is an integer between 7 and 100,000);

(2) reacting the compound prepared in step (1) of Chemical Formula 3 with 0.01 to 1.9 equivalents of an amino acid ester represented by the following Chemical Formula 4 or a salt thereof $$NH_2CH(R^1)CO_2R^2;$$ [Chemical Formula 4]

(3) reacting the compound prepared in step (2) with 0 to 1.9 equivalents of one selected from amino acid, peptide, and depsipeptide ester, represented by the following Chemical Formula 5, and a salt thereof $$NH_2(R^3)(R^4)(R^5);$$ [Chemical Formula 5]

(4) reacting the compound prepared in step (3) with 0.01 to 1.9 equivalents of substituents with a functional group represented by the following Chemical Formula 6, or a salt thereof $$NH_2(R^6)(R^7)(R^8); \text{ and}$$ [Chemical Formula 6]

(5) reacting the compound prepared in step (4) with 0.01 to 1.9 equivalents of aminomethoxy polyethyleneglycol represented by the following Chemical Formula 7, or a salt thereof $$NH_2(CH_2CH_2O)_pCH_3; \text{ and} \quad \text{[Chemical Formula 7]}$$

when $R^8$ is $CH_2C_6H_5$ or $CH_2CHCH_2$ in Chemical Formula 6, the preparation method of the present invention may additionally include the step (5-1) of dehydrogenating (when $R^8$ is $CH_2C_6H_5$), or de-allylesterifying (when $R^8$ is $CH_2CHCH_2$) the polymer prepared in step (5), to prepare the poly(organophosphazene) in which $R^9$ has a hydrogen functional group.

Moreover, the preparation method of the present invention may additionally include the step (5-2) of reacting the product of step (5) or (5-1) with lysine, arginine, cystein, thiol alkylamine, polyethyleneimines, polylysines, polyarginines, or protamines having various molecular weights, to prepare the poly(organophosphazene) in which $R^9$ has various functional groups selected from the group consisting of $NHCH(SH)CO_2H$, $NH(CH_2)_qSH$, $NH(CH_2CH_2NH)_rH$, $[NH(CH_2)_4-CH(NH_2)CO]_rOH$, $[NHC(=NH)(CH_2)_3CH(NH_2)CO]_rOH$, and protamines.

Moreover, the preparation method of the present invention may include the step (6) of reacting the compound prepared in step (5), step (5-1) or step (5-2) with bioactive molecules ($R^{10}$). $R^{10}$ is selected from the group consisting of paclitaxel, doxorubicin, camptothecin, epirubicine, 5-fluorouracil, 10-hydroxycamptothecin, 10-aminocamptothecin, 7-ethyl-camptothecin, irinotecan, methotrexate, mitomycin C, taxoid, docetaxel, chlorambucil, calicheamicin, maytansinoid, 2-pyrrolino-doxorubicin (AN-201), daunorubicin, butyric acid, melphalan, 4'-dimethyldeoxypodophyllotoxin, curcumin, podophyllotoxin, epipodophyllotoxin, 4-β-amino-4'-O-demethylepipodophyllotoxin, tallysomycin S10b, daunomycin, duocarmycin A, duocarmycin SA, cis-aconityl-daunomycin, calicheamicin, diazeniumdiolate, netropsin, 6-metcaptopurine, glucuronidation, phosmidosine, streptonigrin, hematoporphyrin, desferrioxamine (DFO), deferiprone, acivicin, estramustine, enediyne, arginine-glycin-aspatic acid peptide, neuropeptides [such as neurotensin, tachykinin, neuropeptide Y (NPY), peptide YY (PYY), vasoactive intestinal polypeptide (VIP), and pituitray adenylate cyclase-activating polypeptide (PACAP)], albumin, Bovin serum albumin (BSA), bovin pancreatic ribonuclease (RNase A), Bovin seminal ribonuclease (BS-RNase), Bowman-birk protease inhibitor (BBI), collagen, fibronetin, laminin, erythropoietin (EPO), interferon, hirudin, colony stimulating factor (CSF), insulin, desmopressin, glucagon-like peptide 1 (GLP1), human growth hormone antagonist, tumor necrosis factor receptor 1 (TNFR1), asparaginase, adenosine deaminase, growth factors [such as bone morphogenetic proteins (BMPs), fibroblast growth factor (FGF), vascular endothelial growth factor (VEGF), epidermal growth factor (EGF), nerve growth factor (NGF), platelet derived growth factor (PDFG), insulin like growth factor (IGF), transforming growth factor-beta (TGF-β), brain-derived neurotrophic factor (BDNF), neurotrophin-2 (NT-3) and neurotrophin-4/5 (NT-4/5)], tumor necrosis factor-related apoptosis-inducing ligand (TRAIL), cytokines [such as interferon-alpha 1a (IFN-α 1a), interferon-alpha 2a (IFN-α 2a), interferon-alpha 2b (IFN-α2b), interferon-gamma (IFN-γ), interleukin-1 (IL-1), interleukin-2 (IL-2), interleukin-3 (IL-3), interleukin-4 (IL-4), interleukin-5 (IL-5) and interleukin-6 (IL-6), tumor necrosis factor-alpha (TNF-α) and leukemia-inhibitory factor (LIF)], theanine dexamethason, heparin, chitosan, hyaluronan, cyclodextran, starch, carbohydrate, saccharide, fluorescent protein [such as green fluorescent protein (GFP) and red fluorescent protein (RFP)], virus-like particle (VLP), and vaccine, According to step (6), the preparation method of the present invention may obtain the poly(organophosphazene)-bioactive molecule conjugates in which the bioactive molecule is chemically bonded with the poly(organophosphazene) directly.

The above preparation process of the poly(organophosphazene) conjugated with drugs or bioactive molecules of Chemical Formula 1 is summarized in Reaction Formula 1:

[Reaction Formula 1]

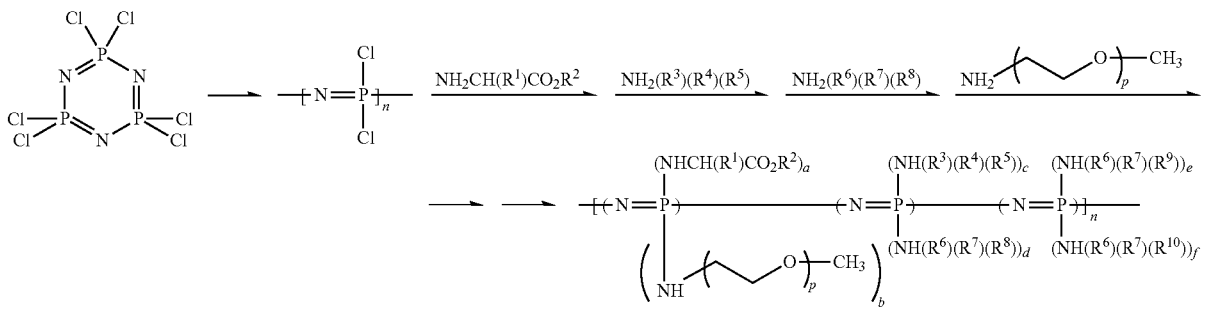

In the Chemical Formula 4, 5, 6, and 7 and the Reaction Formula 1, $R^1$, $R^2$, $R^3$, $R^4$, $R^5$, $R^6$, $R^7$, $R^8$, $R^9$, $R^{10}$, $a_1$, $a_2$, b, c, d, e, f, n, and p are the same as defined for Chemical Formula 1.

Hereinafter, the preparation method of the poly(organophosphazene)-bioactive molecule conjugates of Chemical Formula 1 will be explained more in detail, but is not limited thereby.

All preparing reaction processes may preferably use a vacuum and/or a nitrogen line to prevent moisture from being flowed in. Further, it is preferable that all solvents used in the reaction are used after sufficiently removing moisture therein by conventional methods.

Firstly, step (1) may be performed by putting the compound of Chemical Formula 2 and 0.1 to 10 wt % of $AlCl_3$ into a glass reaction tube, and after hermetically sealing the tube, reacting at 200 to 250° C. for 4 to 8 hours while stirring at 1 rpm (rotations per minute).

Step (2) may be performed by reacting 1 equivalent of the product of step (1) under the presence of 0.01 to 1.9 equivalents of amino acid ester of Chemical Formula 4 or its salt and 4 equivalents of triethylamine. Preferably, the salt of the amino acid ester of Chemical Formula 4 may be sulfate or chlorohydrate. The reaction solvent may be selected from the group consisting of tetrahydrofuran, dioxane, chloroform and toluene, but is not limited thereby. The reaction may be performed at −60° C. to 50° C. for about 8 to 72 hours.

Step (3) may be performed by reacting 1 equivalent of the product of step (2) under the presence of 0 to 1.9 equivalents of amino acid, peptide, depsipeptide ester, as represented by Chemical Formula 5, or a salt thereof, and 4 equivalents of triethylamine. Preferably, said salt of the compound of Chemical Formula 5 may be oxalate, chlorohydrate, or trifluoro acid salt. The reaction solvent may be selected from the group consisting of acetonitrile, tetrahydrofuran, dioxane, chloroform, and toluene, but is not limited thereby. The reaction may be performed at 0° C. to 50° C. for about 1 to 72 hours.

Step (4) may be performed by reacting 1 equivalent of the product of step (3) under the presence of 0.01 to 1.9 equivalents of the substituent with a functional group of Chemical Formula 6 or its salt and 4 equivalents of triethylamine. Preferably, said salt of the substituent of Chemical Formula 6 may be oxalate, chlorohydrate, or trifluoro acid salt. The reaction solvent may be selected from the group consisting of acetonitrile, tetrahydrofuran, dioxane, chloroform, and toluene, but is not limited thereby. The reaction may be performed at 25° C. to 50° C. for about 12 to 72 hours.

Step (5) may be performed by reacting the product of step (4) under the presence of 2 equivalents (based on the amount of remaining chlorine groups) of aminomethoxy polyethyleneglycol of Chemical Formula 6 and 4 equivalents of triethylamine to substitute all the remaining chlorine groups, wherein the equivalent is calculated based on the remaining chlorine groups. The reaction solvent may be selected from the group consisting of tetrahydrofuran, dioxane, chloroform, and toluene, but is not limited thereby. The reaction may be performed at 25° C. to 50° C. for about 24 to 72 hours.

When $R^8$ is $CH_2C_6H_5$ in Chemical Formula 6, step (5-1) may be performed by dehydrogenating the product of step (5) under the presence of 50 to 90 wt % of palladium/charcoal or palladium black and hydrogen gas (pressure range from 30 to 80 psi), to be substituted with a carboxylic acid group. The reaction solvent may be methylalcohol or ethylalcohol, but is not limited thereby. The reaction may be performed at 10° C. to 35° C. for about 1 to 24 hours.

When $R^8$ is $CH_2CHCH_2$ in Chemical Formula 6, the step (6) may be performed by de-allylesterificating the product of step (5) under the presence of 10 to 20 mol % of tetrakistriphenylphosphine palladium (0) and 10 to 20 equivalents of morpholine, to be substituted with a carboxylic acid group. The reaction solvent may be selected from the group consisting of tetrahydrofuran, dioxane, chloroform, and toluene, but is not limited thereby. The reaction may be performed at 0° C. to 25° C. for about 1 to 24 hours.

Step (5-2) may be performed by reacting the product with the carboxylic acid obtained in step (5) or step (5-1) with one or more selected from lysine, arginine, cystein, thiol alkylamine, polyethyleneimine, polylysine, polyarginines, and protamine having various molecular weights under the presence of 1 to 3 equivalents of dicyclohexyl carbodiimide and 1 to 3 equivalents of hydroxy succinimide, to prepare the poly (organophosphazene) with various functional groups. The reaction solvent may be tetrahydrofuran or chloroform, but is not limited thereby. The reaction may be performed at 0° C. to 25° C. for about 1 to 48 hours.

Step (6) may be performed by reacting the product with the carboxylic acid obtained in step (5), step (5-1) or step (5-2) with the bioactive molecule including a drug having hydroxyl group under the presence of 1 to 3 equivalents of dicyclohexyl carbodiimide and 1 to 3 equivalents of dimethylaminopyridine, to prepare the poly(organophosphazene)-bioactive molecule conjugates in which the bioactive molecule, such as a drug, is chemically bonded in the poly(organophosphazene). The reaction solvent may be dichloromethane, but is not limited thereby. The reaction may be performed at 0° C. to 25° C. for about 1 to 48 hours.

Moreover, step (6) may be performed by reacting the product with the carboxylic acid obtained in step (5), step (5-1) or step (5-2) with the bioactive molecule including a drug having amine group under the presence of 1 to 3 equivalents of tributylamine and 1 to 3 equivalents of isobutylchloroformate, to prepare the poly(organophosphazene)-bioactive molecule conjugates in which the bioactive molecule, such a drug, is chemically bonded in the poly(organophosphazene). The reaction solvent may be tetrahydrofuran, but is not limited thereby. The reaction may be performed at 0° C. to 25° C. for about 1 to 48 hours.

For the step (6), the bioactive molecule having the specific functional group can combine with a functional group on the product having the various functional groups of the step (5), step (5-1) or step (5-2) through the sulfation bind [Int. J. Cancer, 73, 859-864 (1997)], cabamite bind [I. Biochem. Pharmacol, 34, 289 (1985)], or hydrazone bond [J. Control Release, 73, 89-102 (2001)].

In said steps (1) to (5-2), the product of each step may be used in the following step without purification. The pure product may be collected from the reaction mixture of steps (6) through a purification process as follows:

First, the reaction mixture is centrifuged or filtered to remove the precipitate (for example, triethylammonium chloride, triethylammonium salt of oxalic acid, and the like) therefrom. Then, a decompression concentration is performed until only a little solvent remains. The obtained concentrated product is dissolved in tetrahydrofuran, and an excess of ethyl ether, hexane, or a mixed solvent of ethyl ether and hexane is added thereto to induce precipitation. Then, the precipitate is filtered 2 or 3 times to remove the non-reactive substituents. The compound obtained through these processes is dissolved again in a small amount of methylalcohol or ethylalcohol. Then, the reaction product is dialyzed with methylalcohol or ethylalcohol at 25° C. for 3 to 10 days, and then with distilled water at 4° C. to 25° C. for 3 to 10 days. Then, the reaction product is dried under a low temperature, to obtain the pure compound as represented by Chemical Formula 1.

In another aspect, the present invention provides a polymer solution (hydrogel) containing a solution of the poly(organophosphazene)-bioactive molecule conjugates represented by Chemical Formula 1, and showing a sol-gel phase transition with change of temperature.

The poly(organophosphazene)-bioactive molecule conjugate as represented by Chemical Formula 1 show a clear sol-gel phase transition in the solution state dissolved in the proper solvent with change of temperature, is made as gelphase in the body temperature range, and get to do with the gel formation of 3D in the internal injection The hydrogel of the present invention having biodegradability and sol-gel phase transition which depends on the temperature change may be a solution wherein 1 to 50 wt %, preferably from 3 to 20 wt %, of the poly(organophosphazene)-bioactive molecule conjugates of Chemical Formula 1 is dissolved in a solvent selected from the group consisting of water, buffer solution, acid solution, basic solution, salt solution, saline solution, water for injection, and glucose salt solution.

The poly(organophosphazene)-bioactive molecule conjugates of the present invention shows a sol-gel phase transition at a temperature of 10° C. to 60° C. Therefore, the poly (organophosphazene) of the present invention can be in a gel-phase under the body temperature range, and thus, can be useful as a delivery material for various bioactive molecules in a body.

In another aspect, the present invention provides a composition for delivery of bioactive molecules containing one or more selected from the group consisting of the poly(organophosphazene)-bioactive molecule conjugates, and the hydrogel containing the poly(organophosphazene)-bioactive molecule conjugates. The composition for delivery of bioactive molecules may contain one or more additive.

In another aspect, the present invention provides a bioactive molecule delivery system containing one or more selected from the group consisting of the poly(organophosphazene)-bioactive molecule conjugates and the hydrogel containing the poly(organophosphazene)-bioactive molecule conjugates, and one or more selected from the group consisting of an additional bioactive molecule, cell and additive for delivering to the site desiring a cell or a drug, and thus provides excellent medicinal effect and cell activity.

The sol-gel phase transition of the poly(organophosphazene)-bioactive molecule conjugates or the poly(organophosphazene) hydrogel may be controlled by addition of various salts, to achieve the desired gel solidity and gelling temperature (Macromolecules 32, 7820, 1999).

When delivering a polypeptide or protein drug, the introduction of proper additives allows the stability of the drug in the hydrogel to be maintained. Further, the chemical bond, including an ionic bond, between the additives and the drug is induced so as to control the release rate of the drug from the hydrogel. Moreover, when delivering therapeutic cells, the activity of the cell after delivery into the body may be increased due to the additives introduced into the hydrogel.

That is, the additives may induce various interactions for the chemical binding including an ionic bond between the poly(organophosphazene)-bioactive molecule conjugates or the poly(organophosphazene) hydrogel and the bioactive molecules, such as drugs, to control the release of the bioactive molecules, and/or increase the activity of the bioactive molecules such as drugs or therapeutic cells inside the body.

The additive may be one or more selected from the group consisting of cationic polymers (having a molecular weight from 200 to 750,000 such as poly-L-arginine, poly-L-lysine, poly(ethyleneglycol), polyethylenimine, chitosan, protamin, and the like; anionic polymers such as poly(N-vinyl-2-pyrrolidone), polyvinylacetate (PVA), hyaluronic acid, chondroitin sulfate, heparin, alginate, and the like; bioavailable materials such as amiloride, procainamide, acetyl-beta-methylcholine, spermine, spermidine, lysozyme, fibroin, albumin, collagen, transforming growth factor-beta (TGF-beta), bone morphogenetic proteins (BMPs), fibroblast growth factor (bFGF), dexamethason, vascular endothelial growth factor (VEGF), fibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M 1944CS, citric acid, glutamic acid, hydroxypropyl methylcellulose, gelatin, isopropyl myristate, Eudragit, tego betain, dimyristoylphosphatidylcholine, scleroglucan, and the like;

organic solvents such as cremophor EL, ethanol, dimethyl sulfoxide, and the like; preservatives such as methylparaben and the like; sugars such as starch, cyclodextrin and derivatives thereof, lactose, glucose, dextran, mannose, sucrose, trehalose, maltose, ficoll, and the like; polyols such as innositol, mannitol, sorbitol, and the like; sugar-containing polyols such as sucrose-mannitol, glucose-mannitoal, and the like; amino acids such as alanine, arginine, glycine, and the like; polymer-containing polyols such as trehalose-PEG, sucrose-PEG, sucrose-dextran, and the like; sugar-containing amino acid such as sorbitol-glycine, sucrose-glycine, and the like; surfactants such as poloxamer of various molecular weights, tween 20, tween 80, triton X-100, sodium dodecyl sulfate (SDS), Brij, and the like; sugar-containing ions such as trehalose-$ZnSO_4$, maltose-$ZnSO_4$, and the like; and bioacceptable salts such as silicate, NaCl, KCl, NaBr, NaI, LiCl, n-$Bu_4$NBr, n-$Pr_4$NBr, $Et_4$NBr, $Mg(OH)_2$, $Ca(OH)_2$, $ZnCO_3$, $Ca_3(PO_4)_2$, $ZnCl_2$, $(C_2H_3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, AgCl, $AuCl_3$, $CuCl_2$, sodium tetradecyl sulfate, dodecyltrimethylammonium bromide, dodecyltrmethylammonium chloride, tetradecyltrimethylammonium bromide, and the like.

In one embodiment of the present invention, the content of the additive is from about $1 \times 10^{-6}$ to 30 wt %, preferably about $1 \times 10^{-3}$ to 10 wt %, based on the total weight of the bioactive molecule delivery composition or the bioactive molecule delivery system. If the content of the additive is lower than the above-mentioned range, the additives cannot exhibit a desired effect. On the other hand, if the content of the additive is higher than the above-mentioned range, the effect and/or the property of the thermosensitive polymer according to the present invention may be deteriorated.

The additionally contained bioactive molecule is one or more selected from the group consisting of proteins, polypeptides, peptides, vaccines, genes, hormones, anti-cancer drugs, and angiogenesis inhibitors.

The proteins, polypeptides, and peptides may be one or more selected from the group consisting of erythropoietin (EPO), interferon-alpha, interferon-beta, interferon-gamma, growth hormone (human, pig, cow, etc.), growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, a substance which is modified or shows the same effect of a drug, ferment, and cytokines.

The vaccine may be one or more selected from the group consisting of hepatitis vaccine.

The gene may be one or more selected from the group consisting of small interference RNA (siRNA), plasmid DNA, and antisense oligodeoxynucleotide (AS-ODN).

The hormone may be one or more selected from the group consisting of testosterone, estradiol, progesterone, prostaglandins and synthetic analogs thereof, and a substance which is modified or shows the same effect of a drug.

The anti-cancer drug may be one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, caliceamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated with protein, and synthetic analogs thereof, and a substance which is modified or shows the same effect of a drug.

The angiogenesis inhibitor may be one or more selected from the group consisting of BMS-275291, Clodronate, 6-deoxy-6-demethyl-4-dedimethylaminotetracycline, Doxycycline, Marimastat, 2-Methoxyestradiol, Squalamine, SU5164, Thalidomide, TNP-470, Combretastatin A4, Soy Isoflavone, Enzastaurin, CC 5013, Celecoxib, ZD 6474, Halofuginone hydrobromide, interferon-alpha, Bevacizumab, AE-941, Interleukin-12, VEFG-trap, Cetuximab, and synthetic analogs thereof, and a substance which is modified or shows the same effect of a drug.

The additionally contained bioactive molecule may be a therapeutic cell, for example, one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

In the case that the composition containing the poly(organophosphazene)-bioactive molecule conjugates of the present invention contains a drug as the bioactive molecule, the content of the drug is from about $1 \times 10^{-8}$ to 50 vol %, preferably about $1 \times 10^{-4}$ to 20 vol % based on the total volume. If the content of the drug is lower than the above-mentioned range, the desired effect of the drug may not be obtained. On the other hand, if the content of the drug is higher than the above-mentioned range, the property of the thermosensitive polymer can be deteriorated.

The composition containing the poly(organophosphazene)-bioactive molecule conjugates of the present invention can be administered into a living body through a route selected from the group consisting of administration from the outer intestinal tract, opthalmological administration, injection into the cartilage tissue, bone tissue, fat tissue or cancer tissue, suction, percutaneous administration, vaginal administration, urethral administration, rectal administration, nasal administration, oral administration, pulmonary administration, ear administration, muscular administration, hypodermic administration, and intravenous administration, and specifically, a local administration such as hypodermic injection, muscular injection, percutaneous administration, or intratumoral administration is preferable.

The composition of the present invention may be easily injected in various forms because of the characteristic of the poly(organophosphazene)s that they exist as the sol phase at room temperature. Especially, the composition of the present invention may be applied locally in the specific desired location, and the release of the conjugated bioactive molecules can easily be controlled because when the composition is injected into the body, the body temperature causes sol-gel phase transition of the bioactive molecules.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLES

In the examples below, the elementary analysis of carbon, hydrogen, and nitrogen for the product was performed by the Advanced Analysis Center in the Korea Institute of Science and Technology using the Perkin-Elmer C, H, N analyzer.

The nuclear magnetic resonance spectrum with hydrogen and phosphorus is respectively measured by using Varian Gemini-300, and the average molecular weight ($M_w$) is measured through gel permeation chromatography using a Waters 1515 pump and a 2410 differentiation refractometer.

During manufacturing reaction processes, the reactants were dried in the vacuum condition and nitrogen line with 50° C. for 2 days in order to the utmost removing the moisture. Moreover, the flasks were dried many times under the vacuum condition. A solvent and additive were dipped through the cannula during manufacturing process.

Example 1

The Preparation of poly[(isoleucineethylester)(aminomethoxypolyethyleneglycol 550)(glycylglycine) (glycylglycylpaclitaxel)phosphazene], [NP (IleOEt)$_{1.25}$(AMPEG550)$_{0.51}$(GlyGlyCOOH)$_{0.22}$ (GlyGlyPTX)$_{0.02}$]$_n$ Dried isoleucine ethylester chlorohydrate (4.22 g, 21.58 mmol) were dissolved in the anhydrous tetrahydrofuran (THF) 100 ml, triethylamine (6.55 g, 64.74 mmol) were added thereto. Then, the solution was added dropwisely into a dryice-acetone bath at −60° C. containing tetrahydrofuran solution (50 ml) in which poly(dichlorophosphazene)(2.00 g, 17.26 mmol) were dissolved, and then the mixture was reacted at room temperature for 48 hours.

After the reaction rate was confirmed as $^{31}$P-NMR data, dried glycylglycineallylester trifluoro aceticacid salt (1.19 g, 4.14 mmol) were melted in the anhydrous THF 50 ml. Triethylamine (1.26 g, 12.42 mmol) were added thereto, and then the mixture was reacted for 8 hours.

After again the reaction rate was confirmed as $^{31}$P-NMR data, the solution which dried aminomethoxypolyethyleneglycol (9.68 g, 17.61 mmo, $M_w$=550) melted in the anhydrous THF (50 ml) was added dropwisely to the reactant. The mixture was reacted at the room temperature for 12 hours and was reacted at 40° C. to 50° C. for 24 hours.

The reaction solution was filtered to remove the generated triethylamine hydrochloride salt. The remaining solution after filtration was concentrated under decompression until the solvent was mostly removed. The obtained concentrate was dissolved in THF (10 ml) and an excess of hexane was added thereto to form precipitation. After the process was repeated 2 or 3 times, the obtained precipitate was again dissolved in a small amount of methylalcohol. The resulting solution was dialyzed by MWCO 12000 Membrane (Spectrum Laboratories, Inc.) with methylalcohol for 5 days at room temperature, and then, with distilled water for 5 days.

After, the resulting product was dried under a low temperature and poly(dichloro phosphazene) [NP(IleOEt)$_{1.25}$(AMPEG550)$_{0.51}$(GlyGlyOAll)$_{0.24}$]$_n$(14.21 g) was obtained.

The obtained [NP(IleOEt)$_{1.25}$(AMPEG550)$_{0.51}$(GlyGlyOAll)$_{0.24}$]$_n$(14.21 g) was melted in the anhydrous THF (200 ml) and then was reacted at the room temperature for 8 hours using tetrakistriphenylphosphine palladium(0) (0.56 g) of 15 mole % and morpholine (4.23 g) of 20 equivalent. The resulting solution was dialyzed by MWCO 6-8000 Membrane (Spectrum Laboratories, Inc.) with methylalcohol for 5 days at room temperature, and then, with distilled water for 5 days at 4° C. After, the resulting product was dried under a low temperature and the intermediate product [NP(IleOEt)$_{1.25}$(AMPEG550)$_{0.51}$(GlyGlCOOH)$_{0.24}$]$_n$(13.78 g) was obtained.

The obtained [NP(IleOEt)$_{1.25}$(AMPEG550)$_{0.51}$(GlyGlyCOOH)$_{0.24}$]$_n$(13.78 g) was melted in anhydrous dichloromethane (100 μm) and was reacted at 0° C. for 24 hours using paclitaxel (0.39 g) of 0.02 equivalent, dicyclohexylcarbodiimide (0.16 g) of 0.04 equivalent, and dimethylaminopyridine (0.01 g) of 0.04 equivalent. The resulting solution was dialyzed by MWCO 6-8000 Membrane (Spectrum Laboratories, Inc.) with methylalcohol for 5 days at room temperature, and then, with distilled water for 5 days at 4° C. After, the resulting product was dried under a low temperature and the end product [NP(IleOEt)$_{1.25}$(AMPEG550)$_{0.51}$(GlyGlyCOOH)$_{0.22}$(GlyGlyPTX)$_{0.02}$]$_n$(13.02 g, yield 89%) was obtained.

Empirical Formula: $C_{25}H_{43}N_3O_8P$
Elementary analysis data: C, 55.27; H, 7.83; N, 7.63
Theoretical value: C, 55.45; H, 7.72; N, 7.71
Hydrogen Nuclear Magnetic Resonance Spectrum (DMSO-d$_6$, ppm): δ 0.92 (b, CH$_3$), 0.11 (s, CH$_3$), 1.25 (b, CH$_2$), 1.57 (s, CH$_3$), 1.65 to 1.79 (b, CH), 1.86 (s, CH$_3$), 2.18 (s, CH$_3$), 2.30 (s, CH$_3$), 3.30 (s, CH$_3$), 3.42 to 3.50 (b, CH$_2$), 3.56 (s, CH$_2$), 4.08 (b, CH), 4.15 (b, CH$_2$), 4.65 (t, CH), 4.78 (s, OH), 4.99 (t, CH), 5.22 (s, CH), 5.48 (d, CH), 5.64 (d, CH), 5.96 (t, CH), 6.26 (d, CH), 6.36 (s, OH), 7.28 to 8.04 (m, aromatic compounds), 9.00 (d, NH).
Phosphorus Nuclear Magnetic Resonance Spectrum (DMSO-d$_6$, ppm): δ 17.9
Average molecular weight (M$_w$): 45000

Example 2

The Preparation of poly[(isoleucineethylester)(aminomethoxypolyethyleneglycol 550)(glycylglycine)(glycylglycylpaclitaxel)phosphazene], [NP(IleOEt)$_{1.25}$(AMPEG550)$_{0.55}$(GlyGlyCOOH)$_{0.18}$(GlyGlyPTX)$_{0.2}$]$_n$ The synthesis was conducted by the same method as in Example 1, except that poly(dichloro phosphazene) (2.00 g, 17.26 mmol), isoleucine ethylester (4.22 g, 21.58 mmol), glycylglycineallylester trifluoroaceticacid salt (0.99 g, 3.45 mmol), aminomethoxypolyethyleneglycol having the molecular weight of 550(10.44 g, 18.99 mmol), tetrakistriphenylphosphine palladium(0)(0.61 g), morpholine (4.85 g), paclitaxel (0.40 g), dicyclohexylcarbodiimide (0.17 g), dimethylaminopyridine (0.10 g), triethylamine (7.59 g), tetrahydrofuran (550 ml), and dichloromethane (100 ml) were used, to obtain 6.95 g of the end product [NP(IleOEt)$_{1.25}$(AMPEG550)$_{0.55}$(GlyGlyCOOH)$_{0.18}$(GlyGlyPTX)$_{0.02}$]$_n$ (yield 77%).

Empirical Formula: $C_{30}H_{68}N_8O_{14}P$
Elementary analysis data: C, 47.80; H, 9.20; N, 9.60
Theoretical value: C, 48.21; H, 8.97; N, 9.58
Hydrogen Nuclear Magnetic Resonance Spectrum (DMSO-d$_6$, ppm): δ 0.92 (b, CH$_3$), 0.11 (s, CH$_3$), 1.25 (b, CH$_2$), 1.57 (s, CH$_3$), 1.65 to 1.79 (b, CH), 1.86 (s, CH$_3$), 2.18 (s, CH$_3$), 2.30 (s, CH$_3$), 3.30 (s, CH$_3$), 3.42 to 3.50 (b, CH$_2$), 3.56 (s, CH$_2$), 4.08 (b, CH), 4.15 (b, CH$_2$), 4.65 (t, CH), 4.78 (s, OH), 4.99 (t, CH), 5.22 (s, CH), 5.48 (d, CH), 5.64 (d, CH), 5.96 (t, CH), 6.26 (d, CH), 6.36 (s, OH), 7.28 내지 8.04 (m, aromatic compounds), 9.00 (d, NH).
Phosphorus Nuclear Magnetic Resonance Spectrum (DMSO-d$_6$, ppm): δ 18.2
Average molecular weight (M$_w$): 31000

Example 3

The Preparation of poly[(isoleucineethylester)(aminomethoxypolyethyleneglycol 550)(glycylglycine)(glycylglycyldoxorubicin)phosphazene], [NP(IleOEt)$_{1.20}$(AMPEG550)$_{0.60}$(GlyGlyCOOH)$_{0.10}$(GlyGlyDOX)$_{0.04}$]$_n$ The synthesis was conducted by the same method as in Example 1, except that poly(dichloro phosphazene) (2.00 g, 17.26 mmol), isoleucine ethylester (4.22 g, 21.58 mmol), glycylglycineallylester trifluoroaceticacid salt (0.99 g, 3.45 mmol), aminomethoxypolyethyleneglycol having the molecular weight of 550 (10.44 g, 18.99 mmol), tetrakistriphenylphosphine palladium(0)(0.62 g), morpholine (4.95 g), and triethylamine (7.60 g), tetrahydrofuran (550 ml) were used, to obtain the intermediate product [NP(IleOEt)$_{1.20}$(AMPEG550)$_{0.60}$(GlyGlyCOOH)$_{0.14}$]$_n$ (11.23 g).

The obtained [NP(IleOEt)$_{1.20}$(AMPEG550)$_{0.60}$(GlyGlyCOOH)$_{0.14}$]$_n$ (11.23 g) was melted in the anhydrous tetrahydrofuran (100 ml) and then tributylamine (0.22 g) of 0.08 equivalent and isobutylchloroformate (0.16 g) of 0.08 equivalent were added dropwisely thereto at 0° C. for 30 minutes. Thereafter, doxorubicin (0.44 g) of 0.04 equivalent was melted in the water of the small amount, and the doxorubicin solution was added dropwisely into the activated solution as described in the above, and it was reacted at 0° C. for 1 hour, subsequently was reacted at room temperature for 24 hours.

The resulting solution was dialyzed by MWCO 6-8000 Membrane (Spectrum Laboratories, Inc.) with methylalcohol for 5 days at room temperature, and then, with distilled water for 5 days at 4° C. Then, the resulting product was dried under a low temperature and the end product [NP(IleOEt)$_{1.20}$(AMPEG550)$_{0.60}$(GlyGlyCOOH)$_{0.10}$(GlyGlyDOX)$_{0.04}$]$_n$ (10.02 g, yield 82%) was obtained.

Empirical Formula: $C_{29}H_{70}N_5O_{14}P$
Elementary analysis data: C, 47.01; H, 9.38; N, 9.59
Theoretical value: C, 46.98; H, 8.97; N, 8.98
Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 2.16 (m, CH), 3.42 to 3.50 (b, CH$_2$), 3.56 (s, CH$_2$), 4.08 (b, CH), 4.56 (m, CH), 4.68 (d, CH), 4.85 (m, CH), 4.94 (m, CH), 5.21 (s, CH), 5.45 (s, CH), 6.63 (d, NH), 7.65 (m, CH), 7.92 (d, CH), 4.08 (b, CH).
Phosphorus Nuclear Magnetic Resonance Spectrum (DMSO-d$_6$, ppm): δ 17.9
Average molecular weight (M$_w$): 392000

Example 4

The Preparation of poly[(isoleucineethylester)(aminomethoxypolyethyleneglycol 550)(glycylglycine)(glycylglycyldoxorubicin)phosphazene], [NP(IleOEt)$_{1.24}$(AMPEG550)$_{0.57}$(GlyGlyCOOH)$_{0.14}$(GlyGlyDOX)$_{0.05}$]$_n$ The synthesis was conducted by the same method as in Example 3, except that poly(dichloro phosphazene) (2.00 g, 17.26 mmol), isoleucine ethylester (4.19 g, 21.40 mmol), glycylglycineallylester trifluoroaceticacid salt (0.94 g, 3.28 mmol), aminomethoxypolyethyleneglycol having the molecular weight of 550 (10.82 g, 19.68 mmol), tetrakistriphenylphosphine palladium(0)(0.63 g), morpholine (5.05 g), doxorubicin (0.51 g), isobutylchloroformate (0.19 g), tributylamine (0.26 g), triethylamine (7.49 g), and tetrahydrofuran (650 ml) were used, to obtain 11.25 g of the end product [NP(IleOEt)$_{1.24}$(AMPEG550)$_{0.57}$(GlyGlyCOOH)$_{0.14}$ (GlyGlyDOX)$_{0.05}$]$_n$ (yield 81%).

Empirical Formula: $C_{25}H_{57}N_5O_{11}P$
Elementary analysis data: C, 48.12; H, 9.30; N, 11.26
Theoretical value: C, 49.41; H, 9.63; N, 10.91
Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 2.16 (m, CH), 3.42 to 3.50 (b, CH$_2$), 3.56 (s, CH$_2$), 4.08 (b, CH), 4.56 (m, CH), 4.68 (d, CH), 4.85 (m, CH), 4.94 (m, CH), 5.21 (s, CH), 5.45 (s, CH), 6.63 (d, NH), 7.65 (m, CH), 7.92 (d, CH), 4.08 (b, CH).
Phosphorus Nuclear Magnetic Resonance Spectrum (DMSO-d$_6$, ppm): δ 18.1
Average molecular weight (M$_w$): 91800

Example 5

The Preparation of poly[(isoleucineethylester)(aminomethoxypolyethyleneglycol 550)(glycylglycine) (glycylglycyldoxorubicin)phosphazene], [NP(IleOEt)$_{1.22}$(AMPEG550)$_{0.66}$(GlyGlyCOOH)$_{0.06}$ (GlyGlyDOX)$_{0.06}$]$_n$ The synthesis was conducted using the same method as in Example 3, except that poly(dichloro phosphazene) (2.00 g, 17.26 mmol), isoleucine ethylester (4.12 g, 21.06 mmol), glycylglycineallylester trifluoroaceticacid salt (0.59 g, 2.07 mmol), aminomethoxypolyethyleneglycol having the molecular weight of 550 (12.53 g, 22.78 mmol), tetrakis triphenylphosphin palladium(0) (0.53 g), morpholine (4.78 g), doxorubicin (0.80 g), isobutylchloroformate (0.29 g), tributylamine (0.40 g), triethylamine (7.02 g), and tetrahydrofuran (650 ml) were used, to obtain 13.38 g of the end product [NP(IleOEt)$_{1.22}$(AMPEG550)$_{0.66}$(GlyGlyCOOH)$_{0.06}$(GlyGlyDOX)$_{0.06}$]$_n$ (yield 87%).

Empirical Formula: $C_{26}H_{63}N_5O_{12}P$
Elementary analysis data: C, 46.95; H, 9.48; N, 10.74
Theoretical value: C, 46.21; H, 8.95; N, 10.13
Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 2.16 (m, CH), 3.42 to 3.50 (b, CH$_2$), 3.56 (s, CH$_2$), 4.08 (b, CH), 4.56 (m, CH), 4.68 (d, CH), 4.85 (m, CH), 4.94 (m, CH), 5.21 (s, CH), 5.45 (s, CH), 6.63 (d, NH), 7.65 (m, CH), 7.92 (d, CH), 4.08 (b, CH).
Phosphorus Nuclear Magnetic Resonance Spectrum (DMSO-d$_6$, ppm): δ 19.0
Average molecular weight (M$_w$): 88500

Example 6

The Preparation of poly[(isoleucineethylester)(aminomethoxypolyethyleneglycol 750)(glycylglycine) (glycylglycyldoxorubicin)phosphazene], [NP(IleOEt)$_{1.27}$(AMPEG750)$_{0.57}$(GlyGlyCOOH)$_{0.23}$ (GlyGlyDOX)$_{0.05}$]$_n$ The synthesis was conducted using the same method as in Example 3, except that poly(dichloro phosphazene) (2.00 g, 17.26 mmol), isoleucine ethylester (4.29 g, 21.92 mmol), glycylglycineallylester trifluoroaceticacid salt (1.38 g, 4.83 mmol), aminomethoxypolyethyleneglycol having the molecular weight of 750 (14.76 g, 19.68 mmol), tetrakistriphenylphosphine palladium(0) (0.71 g), morpholine (5.98 g), doxorubicin (0.67 g), isobutylchloroformate (0.24 g), tributylamine (0.34 g), triethylamine (8.12 g), and tetrahydrofuran (650 ml) were used, to obtain 14.95 g of the end product [NP(IleOEt)$_{1.27}$(AMPEG750)$_{0.57}$(GlyGlyCOOH)$_{0.23}$ (GlyGlyDOX)$_{0.05}$]$_n$ (yield 73%).

Empirical Formula: $C_{20}H_{40}N_3O_7P$
Elementary analysis data: C, 50.65; H, 8.64; N, 8.98
Theoretical value: C, 49.49; H, 8.55; N, 8.79
Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 2.16 (m, CH), 3.42 to 3.50 (b, CH$_2$), 3.56 (s, CH$_2$), 4.08 (b, CH), 4.56 (m, CH), 4.68 (d, CH), 4.85 (m, CH), 4.94 (m, CH), 5.21 (s, CH), 5.45 (s, CH), 6.63 (d, NH), 7.65 (m, CH), 7.92 (d, CH), 4.08 (b, CH).
Phosphorus Nuclear Magnetic Resonance Spectrum (DMSO-d$_6$, ppm): δ 19.1
Average molecular weight (M$_w$): 87400

Example 7

The Preparation of poly[(isoleucineethylester)(aminomethoxypolyethyleneglycol 550)(glycylglycine) (glycylglycylglycin-arginine-glycin-asparagine-cerinicacidpeptied)phosphazene], [NP(IleOEt)$_{1.30}$(AMPEG550)$_{0.53}$(GlyGlyCOOH)$_{0.07}$ (GlyGlyGRGDS)$_{0.01}$]$_n$ The synthesis was conducted by the same method as in Example 3, except that poly(dichloro phosphazene) (2.00 g, 17.26 mmol), isoleucine ethylester (4.39 g, 22.44 mmol), glycylglycineallylester trifluoroaceticacid salt (0.84 g, 2.93 mmol), aminomethoxypolyethyleneglycol having the molecular weight of 550 (10.06 g, 18.30 mmol), tetrakistriphenylphosphine palladium(0) (0.48 g), morpholine (4.23 g), glycine-arginine-glycine-asparagine-cerinic acid peptide (0.87 g), isobutylchloroformate (0.06 g), tributylamine (0.62 g), triethylamine (7.70 g), and tetrahydrofuran (650 ml) were used, to obtain 10.87 g of the end product [NP(IleOEt)$_{1.30}$(AMPEG550)$_{0.53}$(GlyGlyCOOH)$_{0.07}$(GlyGlyGRGDS)$_{0.10}$]$_n$ (yield 72%).

The end product, the content of GRGDS was calculated using the protein analysis in the proteomic analysis team of the Korea Basic Science Institute (KBSI).

Empirical Formula: $C_{22}H_{44}N_3O_9P$
Elementary analysis data: C, 50.54; H, 8.50; N, 8.03
Theoretical value: C, 50.50; H, 8.23; N, 7.98
Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 3.42 to 3.50 (b, CH$_2$), 3.56 (s, CH$_2$), 4.08 (b, CH), 4.15 (b, CH$_2$).
Phosphorus Nuclear Magnetic Resonance Spectrum (DMSO-d$_6$, ppm): δ 18.9
Average molecular weight (M$_w$): 108100

Example 8

The Preparation of poly[(isoleucineethylester)(aminomethoxypolyethyleneglycol 550)(glycylglycine) (glycylglycylglycin-arginine-glycin-asparagine-cerinicacidpeptied)phosphazene], [NP(IleOEt)$_{1.13}$(AMPEG550)$_{0.50}$(GlyGlyCOOH)$_{0.04}$ (GlyGlyGRGDS)$_{0.15}$]$_n$ The synthesis was conducted using the same method as in Example 3, except that poly(dichloro phosphazene) (2.00 g, 17.26 mmol), isoleucine ethylester (3.81 g, 19.50 mmol), glycylglycineallylester trifluoroaceticacid salt (0.94 g, 3.28 mmol), aminomethoxypolyethyleneglycol having the molecular weight of 550 (9.49 g, 17.26 mmol), tetrakistriphenylphosphine palladium(0) (0.43 g), morpholine (4.12 g), glycine-arginine-glycine-asparagine-cerinic acid peptide (2.61 g), isobutylchloroformate (0.18 g), tributylamine (1.86 g), triethylamine (6.92 g), and tetrahydrofuran (650 ml) were used, to obtain 11.21 g of the end product [NP(IleOEt)$_{1.13}$(AMPEG550)$_{0.50}$(GlyGlyCOOH)$_{0.04}$(GlyGlyGRGDS)$_{0.15}$]$_n$ (yield 81%).

Empirical Formula: $C_{24}H_{50}N_3O_{10}P$

Elementary analysis data: C, 51.25; H, 8.71; N, 7.21

Theoretical value: C, 50.98H, 8.50 N, 7.92

Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 3.42 to 3.50 (b, CH$_2$), 3.56 (s, CH$_2$), 4.08 (b, CH), 4.15 (b, CH$_2$).

Phosphorus Nuclear Magnetic Resonance Spectrum (DMSO-d$_6$, ppm): δ 19.2

Average molecular weight (M$_w$): 98300

Example 9

The Preparation of poly[(isoleucineethylester)(aminomethoxypolyethyleneglycol 550)(glycylglycine)(glycylglycylglycmethylester)(glycylglycylglycin-arginine-glycin-asparagine-cerinicacidpeptied)phosphazene], [NP(IleOEt)$_{1.19}$(AMPEG550)$_{0.52}$(GlyGlyCOOH)$_{0.10}$(GlyGlyGlyOEt)$_{0.02}$(GlyGlyGRGDS)$_{0.10}$]$_n$ The synthesis was conducted using the same method as in Example 3, except that poly(dichloro phosphazene) (2.00 g, 17.26 mmol), isoleucine ethylester (3.81 g, 19.50 mmol), glycylglycineallylester trifluoroaceticacid salt (0.94 g, 3.28 mmol), aminomethoxypolyethyleneglycol having the molecular weight of 550 (9.49 g, 17.26 mmol), tetrakis triphenylphosphin palladium(0) (0.61 g), morpholine (5.32 g), glycine-arginine-glycine-asparagine-cerinic acid peptide (1.74 g), isobutylchloroformate (0.12 g), tributylamine (1.24 g), triethylamine (7.70 g), and tetrahydrofuran (650 ml) were used, to obtain the intermediate product [NP(IleOEt)$_{1.19}$(AMPEG550)$_{0.52}$(GlyGlyCOOH)$_{0.20}$(GlyGlyGRGDS)$_{0.10}$]$_n$ (13.78 g).

The obtained [NP(IleOEt)$_{1.19}$(AMPEG550)$_{0.52}$(GlyGlyCOOH)$_{0.20}$(GlyGlyGRGDS)$_{0.10}$]$_n$ was melted in the anhydrous tetrahydrofuran (150 ml) and reacted at 0° C. for 1 hour with tributylamine (0.16 g) and the solution that glycylethylester (0.08 g) was melted in the water of the small amount. The resulting solution was dialyzed by MWCO 6-8000 Membrane (Spectrum Laboratories, Inc.) with methylalcohol for 5 days at room temperature, and then, with distilled water for 5 days at 4° C. After, the resulting product was dried under a low temperature and the end product [NP(IleOEt)$_{1.19}$(AMPEG550)$_{0.52}$(GlyGlyCOOH)$_{0.10}$(GlyGlyGlyOEt)$_{0.10}$(GlyGlyGRG DS)$_{0.10}$]$_n$ (13.64 g, yield 91%) was obtained.

Empirical Formula: $C_{25}H_{52}N_3O_{10}P$

Elementary analysis data: C, 51.54; H, 8.77; N, 7.10

Theoretical value: C, 51.87H, 8.51 N, 6.89

Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 3.42 to 3.50 (b, CH$_2$), 3.56 (s, CH$_2$), 4.08 (b, CH), 4.15 (b, CH$_2$).

Phosphorus Nuclear Magnetic Resonance Spectrum (DMSO-d$_6$, ppm): δ 19.1

Average molecular weight (M$_w$): 27200

Example 10

The Preparation of poly[(isoleucineethylester)(aminomethoxypolyethyleneglycol 550)(glycylglycine)(glycylglycylglycyethylester)(glycylglycylglycin-arginine-glycin-asparagine-cerinicacidpeptied)phosphazene], [NP(IleOEt)$_{1.13}$(AMPEG550)$_{0.65}$(GlyGlyGlyOEt)$_{0.17}$(GlyGlyGRGDS)$_{0.05}$]$_n$ The synthesis was conducted using the same method as in Example 3, except that poly(dichloro phosphazene) (2.00 g, 17.26 mmol), isoleucine ethylester (4.36 g, 22.27 mmol), glycylglycineallylester trifluoroaceticacid salt (0.84 g, 2.93 mmol), aminomethoxypolyethyleneglycol having the molecular weight of 550 (10.25 g, 18.64 mmol), tetrakistriphenylphosphine palladium(0) (0.57 g), morpholine (4.98 g), glycine-arginine-glycine-asparagine-cerinic acid peptide (0.79 g), glycylethylester (0.13 g), isobutylchloroformate (0.07 g), tributylamine (0.61 g), triethylamine (7.64 g), and tetrahydrofuran (800 ml) were used, to obtain 12.29 g of the end product [NP(IleOEt)$_{1.29}$(AMPEG550)$_{0.54}$(GlyGlyGlyOEt)$_{0.12}$(GlyGlyGRGDS)$_{0.05}$]$_n$ (yield 80%).

Empirical Formula: $C_{24}H_{47}N_3O_9P$

Elementary analysis data: C, 51.65; H, 8.48; N, 7.60

Theoretical value: C, 50.91; H, 8.30; N, 7.86

Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 3.42 to 3.50 (b, CH$_2$), 3.56 (s, CH$_2$), 4.08 (b, CH), 4.15 (b, CH$_2$).

Phosphorus Nuclear Magnetic Resonance Spectrum (DMSO-d$_6$, ppm): δ 20.0

Average molecular weight (M$_w$): 86500

Example 11

The Preparation of poly[(isoleucineethylester)(aminomethoxypolyethyleneglycol 550)(glycylglycine)(glycylglycin)(glycylglycylglycin-arginine-glycin-asparagine-cerinicacidpeptied)phosphazene], [NP(IleOEt)$_{1.29}$(AMPEG550)$_{0.54}$(GlyGlyCOOH)$_{0.12}$(GlyGlyGRGDS)$_{0.05}$]$_n$ The synthesis was conducted using the same method as in Example 3, except that poly(dichloro phosphazene) (2.00 g, 17.26 mmol), isoleucine ethylester (4.36 g, 22.27 mmol), glycylglycineallylester trifluoroaceticacid salt (0.84 g, 2.93 mmol), aminomethoxypolyethyleneglycol having the molecular weight of 550 (10.25 g, 18.64 mmol), tetrakistriphenylphosphine palladium(0)(0.51 g), morpholine (4.28 g), glycine-arginine-glycine-asparagine-cerinic acid peptide (0.81 g), isobutylchloroformate (0.071 g), tributylamine (0.63 g), triethylamine (7.65 g), and tetrahydrofuran (650 ml) were used, to obtain 16.12 g of the end product [NP(IleOEt)$_{1.29}$ (AMPEG550)$_{0.54}$(GlyGlyCOOH)$_{0.12}$(GlyGlyGRGDY)$_{0.05}$]$_n$ (yield 82%).

Empirical Formula: $C_{23}H_{45}N_3O_9P$

Elementary analysis data: C, 50.63; H, 8.52; N, 7.79

Theoretical value: C, 49.47; H, 8.49; N, 7.70

Hydrogen Nuclear Magnetic Resonance Spectrum (DMSO-d$_6$, ppm): δ 0.92 (b, CH$_3$), 1.25 (b, CH$_2$), 1.57 (s, CH$_3$), 1.65 to 1.79 (b, CH), 3.42 to 3.50 (b, CH$_2$), 3.56 (s, CH$_2$), 4.08 (b, CH), 4.15 (b, CH$_2$).

Phosphorus Nuclear Magnetic Resonance Spectrum (DMSO-d$_6$, ppm): δ 19.1

Average molecular weight ($M_w$): 87400

Example 12

Observation of the Sol-Gel Phase Transition of Poly(Organophosphazene) Conjugated with Drugs or Bioactive Molecules with Change of Temperature The poly(organophosphazene) conjugated with a drug or bioactivemolecules obtained in Examples 1 to 11 were respectively dissolved in phosphate buffered saline (pH 7.4) at 4° C. so as to make solutions with concentrations of 10 wt %. The solutions were put into a chamber of a Brookfield DV-III+ Rheometer equipped with a thermostatic bath (TC-501). The sol-gel phase transition was observed with raising the temperature at the rate of 0.04° C./min and the shear velocity of 0.1 to 1.7 per second.

The gel properties of the thermosensitive poly(organophosphazene) conjugated with a drug or bioactive molecule of the present invention depending on the temperature observed as above are shown in the following Table 2.

Example 13

Observation of the Degree of Weight Loss of the Poly(Organophosphazene) Molecules Conjugated with Paclitaxel According to Lapse of Time The poly(organophosphazene)s conjugated with paclitaxel obtained in the Example 1 and 2 of the present invention were dissolved in phosphate buffered saline (pH 7.4) to make solutions with a concentration of 10 wt %. After the solution (0.5 ml) was put into a millicell to make hydrogel in 37° C., it was dipped in the phosphate buffered saline (10 ml, pH 7.4) in which SDS (0.1 volume %) was included, and then, the solution was put into a bath at 37° C. and stirred at 50 rpm. After the millicell was taken out for the determined time and then was lyophilized, the weight of the poly(organophosphazene)s conjugated with paclitaxel was measured.

Figure 3:
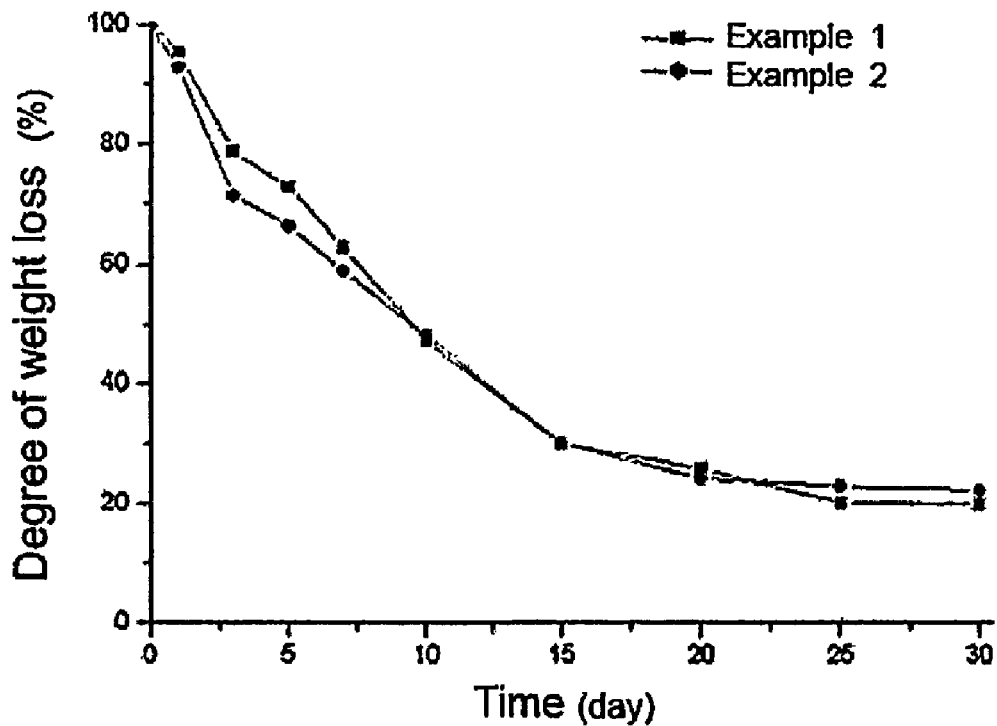
FIG. 3 shows the degree of weight loss of the poly(organophosphazene) conjugated with paclitaxel of the present invention with lapse of time.

The degree of weight loss of the poly(organophosphazene)s conjugated with paclitaxel according to lapse of time is shown in the following FIG. 3. As seen in the FIG. 3,

TABLE 2

| Example | Structure | Max. gelling temp. (° C.)$^a$ | Gel solidity (Pa·s)$^b$ |
|---|---|---|---|
| 1 | [NP(IleOEt)$_{1.25}$(AMPEG550)$_{0.51}$(GlyGlyCOOH)$_{0.22}$(GlyGlyPTX)$_{0.02}$]$_n$ | 40 | 128 |
| 2 | [NP(IleOEt)$_{1.25}$(AMPEG550)$_{0.55}$(GlyGlyCOOH)$_{0.18}$(GlyGlyPTX)$_{0.02}$]$_n$ | 38 | 230 |
| 3 | [NP(IleOEt)$_{1.20}$(AMPEG550)$_{0.60}$(GlyGlyCOOH)$_{0.10}$(GlyGlyDOX)$_{0.04}$]$_n$ | 38 | 158 |
| 4 | [NP(IleOEt)$_{1.24}$(AMPEG550)$_{0.57}$(GlyGlyCOOH)$_{0.14}$(GlyGlyDOX)$_{0.05}$]$_n$ | 37 | 88 |
| 5 | [NP(IleOEt)$_{1.22}$(AMPEG550)$_{0.66}$(GlyGlyCOOH)$_{0.06}$(GlyGlyDOX)$_{0.06}$]$_n$ | 39 | 1477 |
| 6 | [NP(IleOEt)$_{1.27}$(AMPEG750)$_{0.45}$(GlyGlyCOOH)$_{0.23}$(GlyGlyDOX)$_{0.05}$]$_n$ | 46 | 313 |
| 7 | [NP(IleOEt)$_{1.30}$(AMPEG550)$_{0.53}$(GlyGlyCOOH)$_{0.07}$(GlyGlyGRGDS)$_{0.1}$]$_n$ | 42 | 145 |
| 8 | [NP(IleOEt)$_{1.13}$(AMPEG550)$_{0.50}$(GlyGlyCOOH)$_{0.04}$(GlyGlyGRGDS)$_{0.15}$]$_n$ | 39 | 318 |
| 9 | [NP(IleOEt)$_{1.19}$(AMPEG550)$_{0.52}$(GlyGlyCOOH)$_{0.1}$(GlyGlyGlyOEt)$_{0.02}$(GlyGlyGRGDS)$_{0.1}$]$_n$ | 46 | 130 |
| 10 | [NP(IleOEt)$_{1.13}$(AMPEG550)$_{0.65}$(GlyGlyGlyOEt)$_{0.17}$(GlyGlyGRGDS)$_{0.05}$]$_n$ | 42 | 238 |
| 11 | [NP(IleOEt)$_{1.29}$(AMPEG550)$_{0.54}$(GlyGlyCOOH)$_{0.12}$(GlyGlyGRGDY)$_{0.05}$]$_n$ | 44 | 155 |

$^a$(Max. gelling temp.): the temperature where the viscosity of the polymer solution reaches the maximum point
$^b$(Gel solidity): the maximum viscosity of the polymer solution FIG. 1 is a photograph showing the sol-gel phase transition of the poly(organophosphazene) conjugated with paclitaxel of the present invention with temperature change. It shows that at a temperature below the initial gelling temperature, the polymer solution is in the fluid sol-phase, and at the maximum gelling temperature above the initial gelling temperature, it changed into the gel-phase.

Figure 2:
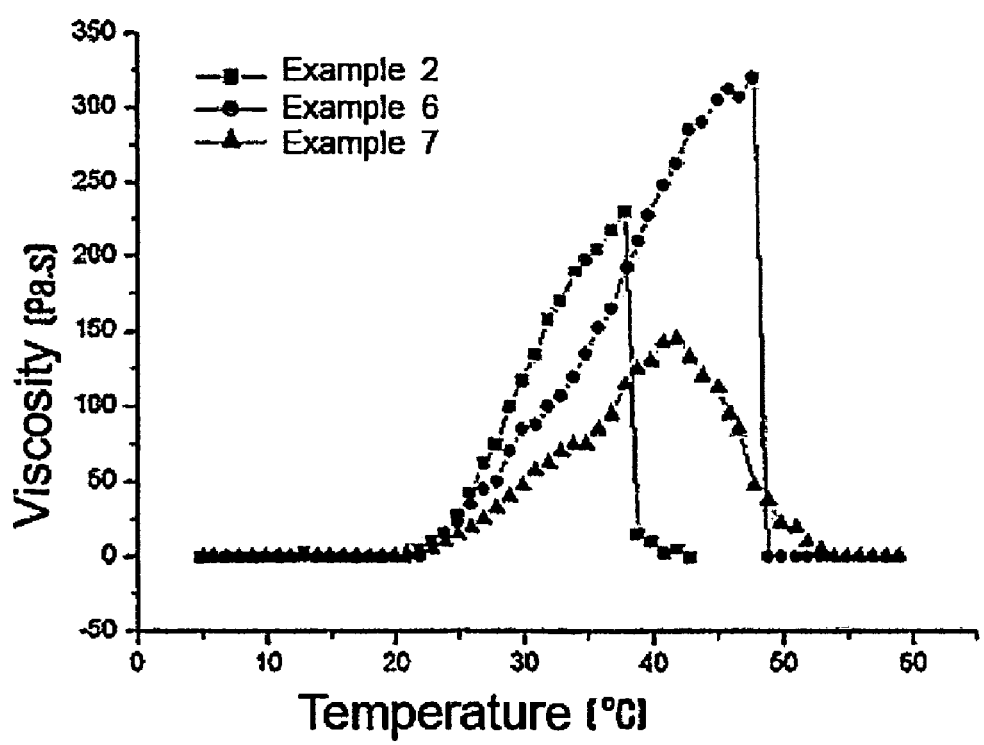
FIG. 2 shows the changes in the viscosity of the poly (organophosphazene) conjugated with anti-cancer drugs or bioactive molecules of the present invention with changes in temperature.

FIG. 2 shows the change in the viscosity of the poly(organophosphazene) conjugated with anti-cancer drugs or bioactive molecules of the present invention with change of temperature.

The poly(organophosphazene)s with a wide range of the maximum gelling temperature and the maximum gel solidity can be confirmed by regulating the kind of the hydrophobic amino acid ester substituted in the polymer, the kind of amino acid, peptide, or depsipeptide capable of controlling the degradation rate, the kind of amino acid or peptide with a functional group, the chain length of methoxypolyethyleneglycol, and the composition of all the substituents (Korean Patent application No. 2006-0005579).

Moreover, the maximum gel strength could be controlled according to the drug substituted in the functional group, the kind of the bioactive molecule, and the degree of substitution. The poly(organophosphazene)s conjugated with drugs or bioactive molecules that are the solution state in the room temperature and the gel phase in the body temperature could be manufactured.

the poly(organophosphazene) hydrogel showed the weight loss of 50% in 10 days, 20% in 30 days in aqueous solution condition (37° C.).

According to analysis of the components of the polymer solution decomposed for a certain time, paclitaxel, phosphates, ammonia, ethylalcohol, and the like, were depected from the polymer solution. Therefore, it can be presumed that the poly(organophosphazene)s conjugated with paclitaxel should be decomposed into ingredients harmless to a living body, such as phosphates, ammonia, ethylalcohol, and the like.

Example 14

Observation of the Degree of Weight Loss of the Poly(Organophosphazene) Conjugated with Doxorubicin or RGD Peptide with Lapse of Time The poly(organophosphazene)s conjugated with doxorubicin obtained in the Example 3 and 4, and the poly(organophosphazene)s conjugated with RGD peptide obtained in the Example 9 of the present invention were respectively dissolved in phosphate buffered saline (pH 7.4) to make solutions with a concentration of 10 wt %, and then, the solutions were put into a bath at 37° C. and stirred at 50 rpm. The degree of hydrolysis of the polymer with time was determined in terms of the degree of the reduced molecular weight of the polymer measured by Gel Permeation Chromatography (GPC) depending on lapse of time.

Figure 4:
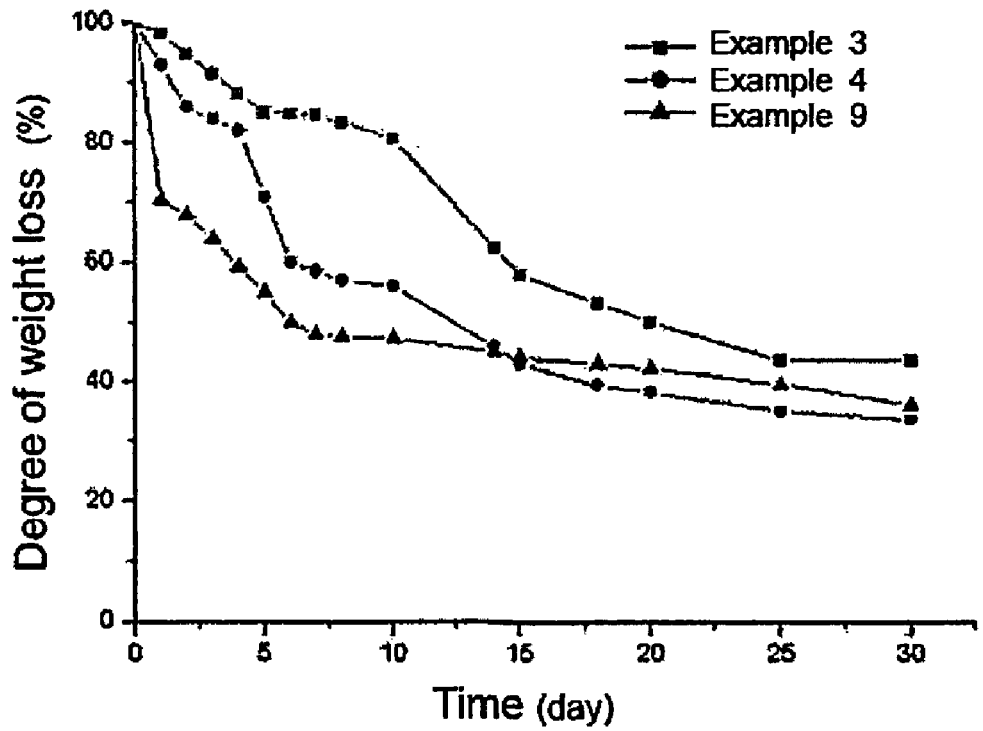
FIG. 4 shows the degree of weight loss of the poly(organophosphazene) conjugated with anti-cancer drugs or bioactive molecules of the present invention with lapse of time.

The degree of weight loss of the poly(organophosphazene)s conjugated with doxorubicin or RGD peptide with lapse of time is shown in the following FIG. 4. As seen in the FIG. 4, the poly(organophosphazene)s conjugated with RGD peptide (Example 9) having the lowest viscosity in 37° C. is the most quickly hydrolyzed. And, The poly(organophosphazene)s conjugated with doxorubicin (Example 3) having the highest viscosity in 37° C. is the most slowly hydrolyzed.

Therefore, in the present invention, the hydrolytic speed of the poly(organophosphazene) conjugated with drugs and bioactive molecules can be controlled by controlling the viscosity of the poly(organophosphazene) at 37° C.

Example 15

Observation of Release Behavior In Vitro of Paclitaxel in the Poly(Organophosphazene) Hydrogel Conjugated with Paclitaxel The poly(organophosphazene) of Example 3 was dissolved in phosphate buffered saline to make a solution having a concentration of 7 wt %. 0.1 vol % of paclitaxel was dissolved in the obtained solution. The solution containing 0.5 ml of paclitaxel was put into a millicell at 37° C. to form a hydrogel.

The obtained poly(organophosphazene) hydrogel containing paclitaxel was added to 100 ml of a release solution. As the release solution, phosphate buffered saline (pH 7.4) containing 0.1 vol % of SDS was used.

The obtained release solution containing the paclitaxel-containing poly(organophosphazene) hydrogel was put into a bath at 37° C., and stirred at 50 rpm. Five (5) ml of the release solution was corrected at regular time intervals as shown in FIG. 4, and the released amount of paclitaxel was measured by HPLC. After correcting 5 ml of the release solution, an equal amount of fresh release solution was supplemented.

Figure 5:
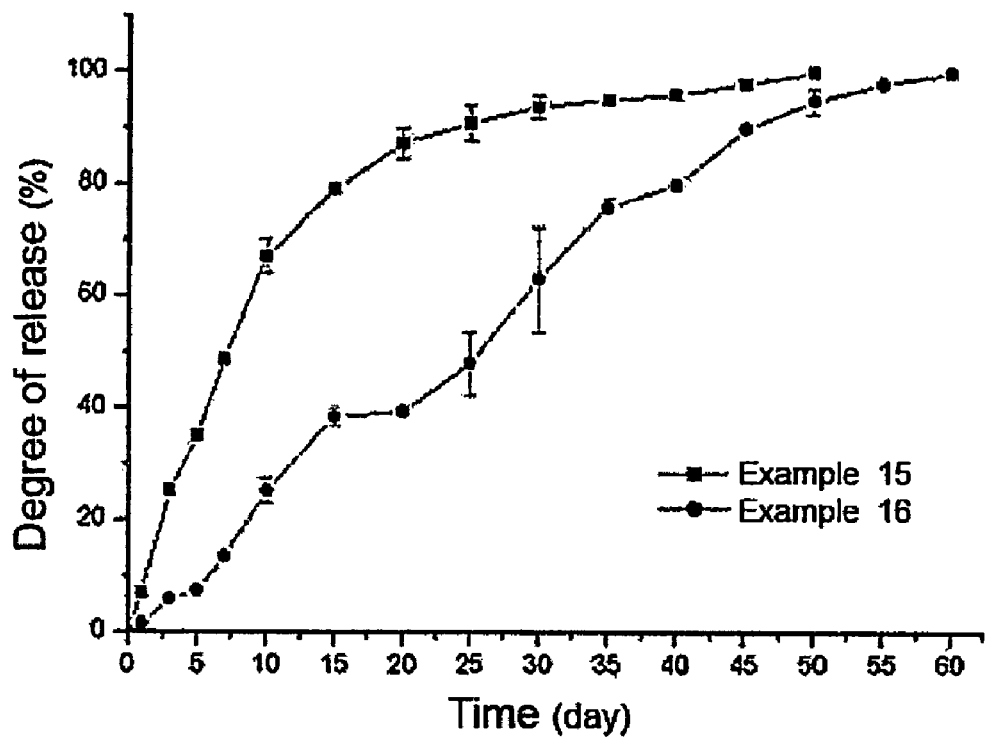
FIG. 5 shows the release behavior of anti-cancer drugs from the poly(organophosphazene) hydrogel conjugated with anti-cancer drugs of the present invention with lapse of time.

The release behavior of paclitaxel in the poly(organophosphazene) hydrogel with time is shown in FIG. 5. As shown in FIG. 5, the release of paclitaxel in the paclitaxel-containing poly(organophosphazene) hydrogel is well controlled and sustained, and the paclitaxel can be released for at least 50 days.

Example 16

Observation of Release Behavior In Vitro of Doxorubicin in the Poly(Organophosphazene) Hydrogel Conjugated with Doxorubicin The poly(organophosphazene) of Example 4 was dissolved in water to make a solution with the concentration of 10 wt %. 0.1 vol % of doxorubicin was dissolved in the obtained solution. The solution containing 0.5 ml of doxorubicin was put into a millicell at 37° C. to form a hydrogel. The obtained poly(organophosphazene) hydrogel containing doxorubicin was added to 10 ml of phosphate buffered saline (pH 7.4) used as a release solution. The obtained release solution containing the doxorubicin-containing poly(organophosphazene) hydrogel was put into a bath at 37° C. and stirred at 50 rpm.

Then, the millicell was transferred into a fresh release solution. The released amount of doxorubicin in the release solution wherein the release of doxorubicin occurs was measured by using UV-VIS spectroscopy (excitation: 495 nm).

The release behavior of doxorubicin in the poly(organophosphazene) hydrogel with time is shown in FIG. 5. As shown in FIG. 5, the release of doxorubicin in the doxorubicin-containing poly(organophosphazene) hydrogel is well controlled and sustained, and the doxorubicin can be released for at least 60 days.

Example 17

Observation of the Anti-Cancer Activity In Vitro of the Poly(Organophosphazene) Conjugated with Anti-Cancer Drug In order to find out anticancer activity in vitro of the poly(organophosphazene) conjugated with anti-cancer drug of the present invention, the trial as follows was performed about the human breast adenocarcinoma (MCF-7, the Korea Cell Line Bank) and the human cervix adenocarcinoma (Hela, the Korea Cell Line Bank).

For the in vitro cell experiment, in order to measure the genesistasis concentration to 50% ($IC_{50}$) toward the cancer cell of the poly(organophosphazene) conjugated with anti-cancer drug, the analytical method using 3-(4,5-dimethylthiazol-2-yl)-2,5-diphenyl-2H-tetrazolium bromide (MTT) was performed [T. Mosmann, J. Immunol. Method, 65, (1985) 55].

The materials for to measuring were respectively melted in the DMSO (dimethylsulfoxide) of the small amount, and they were diluted to the distilled water with 200 times. The materials solution were added to the cancer cell that is MCF-7(the Korea Cell Line Bank) and Hela (the Korea Cell Line Bank). Then, they were added to 96-well microtiter plater to $1.0 \times 10^4$ cell/ml (the concentration of the cancer cell). And they were cultivated for 2, 3, 4 days, respectively, with 37° C. in 5% $CO_2$ condition.

MTT solution (20 µl) was mixed the cultivated cell with, and they were more cultivated for 4 hours with 37° C. in 5% $CO_2$ condition. After the upper culture medium of each cell was removed, DMSO (100 µl) was added to a well and they were shaken in the room temperature to the plate shaker with for 20 minutes, thereby dissolving the formazan crystal generated by reducing of MTT.

The measurement result of anti-cancer activity in vitro of the poly(organophosphazene) conjugated with anti-cancer drug of the present invention was shown in Table 3.

TABLE 3

| Measurement substance | Anti-cancer activity (µg/ml) [$IC_{50}$][a] | | | | | |
|---|---|---|---|---|---|---|
| | MCF-7[b] | | | Hela[c] | | |
| | 2nd day | 3rd day | 4th day | 2nd day | 3rd day | 4th day |
| paclitaxel | 0.022 | 0.006 | 0.002 | 0.083 | 0.021 | 0.014 |
| Example 1 | 0.025 | 0.018 | 0.003 | 0.099 | 0.057 | 0.022 |
| Example 2 | 0.027 | 0.021 | 0.007 | 0.082 | 0.079 | 0.048 |
| doxorubicin | 2.295 | 1.691 | 1.004 | 0.321 | 0.692 | 0.190 |
| Example 3 | 2.294 | 0.926 | 0.798 | 1.477 | 1.065 | 0.605 |
| Example 4 | 2.829 | 2.801 | 1.641 | 1.425 | 0.892 | 0.283 |

[a]$IC_{50}$: the genesistasis concentration toward the cancer cell to 50%
[b]MCF-7: the human breast adenocarcinoma
[c]Hela: the human cervix adenocarcinoma As shown in table 3, the poly(organophosphazene) conjugated with paclitaxel showed anticancer activity in vitro which was similar to that of paclitaxel. And the poly(organophosphazene) conjugated with doxorubicin showed anticancer activity in vitro which was similar to that of doxorubicin.

Example 18

Observation of the Anti-Cancer Activity In Vivo of the Poly(Organophosphazene) Hydrogel Conjugated with Paclitaxel The anti-cancer activity in vivo of the poly(organophosphazene) hydrogel conjugated with paclitaxel prepared by the method of Example 1 was determined by the following method.

A nude mouse (OrientalBio, Balb/C, female of 5-weeks old, 20 g) was used as an animal model for animal experimentation for an in vivo test. Cells of stomach cancer, SNU-601 ($1\times10^7$ cells, 0.2 ml, the Korean Cell Line Bank), were injected into the dorsum of the mouse. A polymer solution containing the 10 wt % poly(organophosphazene)-paclitaxel conjugate of Example 1 in phosphate buffered saline (pH 7.4) was prepared. 0.1 ml and 0.2 ml of the solution were respectively injected into the cancer cells, and the change in the size of the cells was measured.

When the solution is injected in an amount as much as 0.1 ml, the amount of paclitaxel injected is 10 mg per 1 kg of the mouse weight. When the solution is injected in an amount as much as 0.2 ml, the amount of paclitaxel injected is 30 mg per 1 kg of the mouse weight.

As the control group, the magnitude transition of the cancer cell into which paclitaxel was injected in the amount of 60 mg per 1 kg of the mouse weight and that of the cancer cell into which saline was administered instead of the anti-cancer drug were measured respectively. The number of mouse used was 10 heads respectively.

Figure 6:
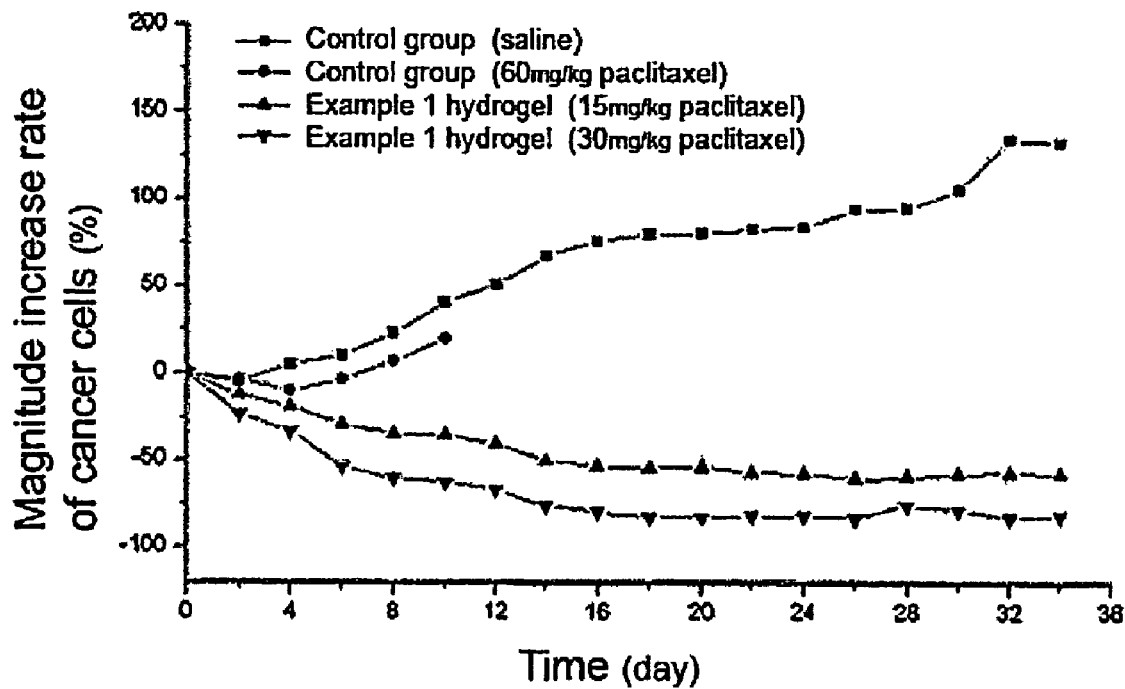
FIG. 6 shows the anti-cancer activity in vivo of the poly(organophosphazene) hydrogel conjugated with paclitaxel of the present invention.

The magnitude transition of the cancer cell measured as above-described is shown in FIG. 6.

As shown in FIG. 6, the cell size of the control group which a saline administered instead of the anti-cancer drug to the cancer cell was increased to 94% after 26 days, and increased to 134% after 34 days.

But the size of the cancer cells of the group to which the poly(organophosphazene) hydrogel conjugated with paclitaxel administered in the amount of 0.1 ml was decreased to 60% after 26 days, and decreased to 57% after 34 days. And the size of the cancer cell of the group to which the poly(organophosphazene) hydrogel conjugated with paclitaxel administered in the amount of 0.2 ml was decreased to 81% after 26 days, and decreased to 81% after 34 days.

As to the control group which a paclitaxel injected to the concentration of 60 mg/kg, 8 mouse heads died after 10 days due to the toxicity of paclitaxel.

Example 19

Observation of the Anti-Cancer Activity In Vivo of the Poly(Organophosphazene) Hydrogel Conjugated with Doxorubicin The anti-cancer activity in vivo of the poly(organophosphazene) hydrogel conjugated with doxorubicin prepared by the method of Example 5 was determined by the following method.

A nude mouse (OrientalBio, Balb/C, female of 5-weeks old, 20 g) was used as an animal model for animal experimentation for an in vivo test. Stomach cancer cells, SNU-601 ($1\times10^7$ cells, 0.2 ml, the Korean Cell Line Bank), were injected into the dorsum of the mouse. A polymer solution containing the 10 wt % poly(organophosphazene)-doxorubicin conjugate of Example 5 in phosphate buffered saline (pH 7.4) was prepared. 0.1 ml and 0.2 ml of the solution was respectively injected into the cancer cells, and the change in the size of the cancer cells was measured.

When the solution is injected in an amount as much as 0.1 ml, the amount of doxorubicin injected is 30 mg per 1 kg of the mouse weight. When the solution is injected in an amount as much as 0.2 ml, the amount of doxorubicin injected is 60 mg per 1 kg of the mouse weight.

As the control group, the magnitude transition of the cancer cell into which doxorubicin was injected in the amount of 30 mg per 1 kg of the mouse weight and that to which saline is administered instead of the anti-cancer drug were measured respectively. The number of mouse used was 10 heads respectively.

Figure 7:
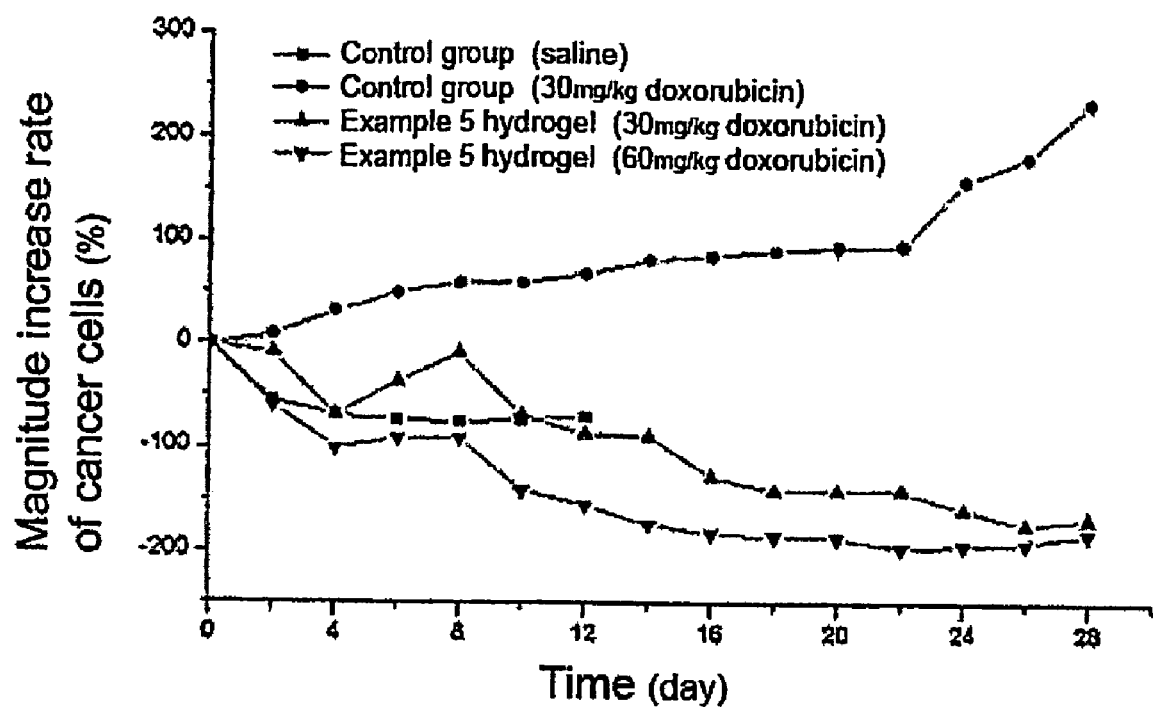
FIG. 7 shows the anti-cancer activity in vivo of the poly(organophosphazene) hydrogel conjugated with doxorubicin of the present invention.

The magnitude transition of the cancer cell measured as above-described was shown in FIG. 7.

As shown in FIG. 7, the cell size of the control group which a saline administered instead of the anti-cancer drug to the cancer cell was increased to 70% after 14 days, and increased to 223% after 28 days.

But the size of the cancer cell of the group to which the poly(organophosphazene) hydrogel conjugated with doxorubicin was administered in the amount of 0.1 ml was decreased to 68% after 14 days, decreased to 173% after 26 days and decreased to 168% after 28 days. And the size of the cancer cells of the group to which the poly(organophosphazene) hydrogel conjugated with doxorubicin administered in the amount of 0.2 ml was decreased to 155% after 14 days, decreased to 195% after 22 days and decreased to 182% after 28 days.

As to the control group, where a doxorubicin was injected in the concentration of 30 mg/kg, all of mouse died after 14 days due to the toxicity of paclitaxel. However, the mouse of the group to which the poly(organophosphazene) hydrogel conjugated with doxorubicin having the doxorubicin concentration of 30 mg/kg with 60 mg/kg were injected did not die.

As described in the above, the drug delivery system of the present invention has excellent drug stability in the drug composition, a long lasting drug release, and excellent biological activity. Therefore, the drug delivery system of the present invention is expected to be useful as a drug carrier and, at the same time, applicable to various biomaterial fields relating to histotechnology.

What is claimed is:

1. A poly(organophosphazene)-bioactive molecule conjugate in which a biodegradable and thermosensitive poly(organophosphazene) with a functional group represented by the following Chemical Formula 1 and a bioactive molecule represented by the following substituent $R^{10}$ are combined:

[Chemical Formula 1]

$$\left[ \left( N=P \right) \left( N=P \frac{(NHCH(R^1)CO_2R^2)_a}{(NH \leftarrow \sim O \rightarrow_p CH_3)_b} \right) \left( N=P \frac{(NH(R^3)(R^4)(R^5))_c}{(NH(R^6)(R^7)(R^8))_d} \right) \left( N=P \frac{(NH(R^6)(R^7)(R^9))_e}{(NH(R^6)(R^7)(R^{10}))_f} \right) \right]_n$$

wherein, p is an integer between 7 and 50, $R^1$ is selected from the group consisting of H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2NH_2C_6H_4$, $OCOC_4N^+H_9$, $CO_2C_2H_5$, $CH_2CO_2C_2H_5$, $(CH_2)_2CO_2C_2H_5$, and $HCONHCH(CH_2C_6H_5)$, $R^2$ is selected from the group consisting of $CH_3$, $C_3H_7$, $C_4H_9$, $C_2H_5$, $CH_2C_6H_5$, and $CH_2CHCH_2$, $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^6$ is CH(Y), $R^7$ is selected from the group consisting of $C_2H_4$, $C_3H_6$, $C_4H_8$, $CH_2C_6H_4$, O, CONHCH(Z)O, CO, S, CONHCH(Z)S, N, CONHCH(Z)N, CON, COCHNH(Z)CON, and CONHCH(Z)CO, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups as defined in Table 1 described in the detailed description of the present application, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamines, q is an integer between 1 and 20, r is an integer between 1 and 18000, $R^{10}$ is selected from the group consisting of paclitaxel, doxorubicin, camptothecin, epirubicine, 5-fluorouracil, 10-hydroxycamptothecin, 10-aminocamptothecin, 7-ethylcamptothecin, irinotecan, methotrexate, mitomycin C, taxoid, docetaxel, chlorambucil, calicheamicin, maytansinoid, 2-pyrrolino-doxorubicin (AN-201), daunorubicin, butyric acid, melphalan, 4'-dimethyldeoxypodophyllotoxin, curcumin, podophyllotoxin, epipodophyllotoxin, 4-β-amino-4'-O-demethylepipodophyllotoxin, tallysomycin S10b, daunomycin, duocarmycin A, duocarmycin SA, cis-aconityl-daunomycin, calicheamicin, diazeniumdiolate, netropsin, 6-metcaptopurine, glucuronidation, phosmidosine, streptonigrin, hematoporphyrin, desferrioxamine (DFO), deferiprone, acivicin, estramustine, enediyne, arginine-glycin-aspatic acid peptide, neuropeptides, albumin, Bovin serum albumin (BSA), bovin pancreatic ribonuclease (RNase A), Bovin seminal ribonuclease (BS-RNase), Bowman-birk protease inhibitor (BBI), collagen, fibronetin, laminin, erythropoietin (EPO), interferon, hirudin, colony stimulating factor (CSF), insulin, desmopressin, glucagon-like peptide 1(GLP1), human growth hormone antagonist, tumor necrosis factor receptor 1(TNFR1), asparaginase, adenosine deaminase, transforming growth factor-beta(TGF-beta), bone morphogenetic proteins (BMPs), growth factors, tumor necrosis factor-related apoptosis-inducing ligand (TRAIL), cytokines, theanine dexamethason, heparin, chitosan, hyaluronan, cyclodextran, starch, carbohydrate, saccharide, fluorescent protein (such as green fluorescent protein(GFP), red fluorescent protein (RFP)), virus-like particle (VLP), and vaccine, a, b, c, d, e, and f respectively represent the content of each substituent, wherein a, b, d, and f are independently from 0.01 to 1.9, c and e are independently from 0 to 1.9, and a+b+c+d+e+f=2.0, and n is from 5 to 100000.

2. The poly(organophosphazene)-bioactive molecule conjugate according to claim 1, selected from the group consisting of poly[(isoleucineethylester)(aminomethoxypolyethyleneglycol 550)(glycylglycine)(glycylglycylpaclitaxel)phosphazene], poly[(isoleucineethylester)(aminomethoxypolyethyleneglycol 550)(glycylglycine)(glycylglycyldoxorubicin)phosphazene], poly[(isoleucineethylester)(aminomethoxypolyethyleneglycol 550)(glycylglycine)(glycylglycylglycin-arginine-glycin-asparagine-cerinicacidpeptied)phosphazene], poly[(isoleucineethylester)(aminomethoxypolyethyleneglycol 550)(glycylglycine)(glycylglycylglycinethyl-ester) (glycylglycylglycin-arginine-glycin-asparagine-cerinicacidpeptied)phosphazene], and poly[(isoleucineethylester)(aminomethoxypolyethyleneglycol 550)(glycylglycine)(glycylglycylglycin-arginine-glycin-asparagine-tyrosinicacidpeptied)phosphazene].

3. A preparation method of the poly(organophosphazene)-bioactive molecule conjugate according to claim 1 comprising the steps of:

(1) thermopolymerizing a phosphazene trimer represented by the following Chemical Formula 2, to prepare a linear polymer of dichloro phosphazene represented by the following Chemical Formula 3

[Chemical Formula 2]

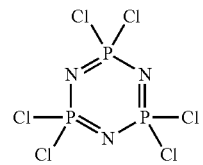

[Chemical Formula 3]

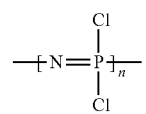

(wherein n is an integer between 7 and 100,000);

(2) reacting the compound prepared in step (1) of Chemical Formula 3 with 0.01 to 1.9 equivalents of an amino acid ester represented by the following Chemical Formula 4 or a salt thereof $NH_2CH(R^1)CO_2R^2$;  [Chemical Formula 4]

(3) reacting the compound prepared in step (2) with 0 to 1.9 equivalents of one selected from amino acid, peptide, and depsipeptide ester, represented by the following Chemical Formula 5, and a salt thereof $NH_2(R^3)(R^4)(R^5)$;  [Chemical Formula 5]

(4) reacting the compound prepared in step (3) with 0.01 to 1.9 equivalents of substituents with a functional group represented by the following Chemical Formula 6, or a salt thereof NH$_2$(R$^6$)(R$^7$)(R$^8$);   [Chemical Formula 6]

(5) reacting the compound prepared in step (4) with 0.01 to 1.9 equivalents of aminomethoxy polyethylene glycol represented by the following Chemical Formula 7, or a salt thereof NH$_2$(CH$_2$CH$_2$O)$_p$CH$_3$; and   [Chemical Formula 7]

(6) reacting the compound prepared in step (5) with a bioactive molecule selected from the group consisting of proteins, polypeptides, peptides, vaccines, genes, hormones, anti-cancer drugs, and angiogenesis inhibitors wherein, p is an integer between 7 and 50;

R$^1$ is selected from the group consisting of H, HCH$_2$, CH$_3$, C$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, CH$_2$C$_2$NH$_2$C$_6$H$_4$, OCOC$_4$N$^+$H$_9$, CO$_2$C$_2$H$_5$, CH$_2$CO$_2$C$_{2H5}$, (CH$_2$)$_2$CO$_2$C$_2$H$_5$, and HCONHCH(CH$_2$C$_6$H$_5$), and R$^2$ is selected from the group consisting of CH$_3$, C$_3$H$_7$, C$_4$H$_9$, C$_2$H$_5$, CH$_2$C$_6$H$_5$, and $_{CH2}$CHCH$_2$;

R$^3$ is CH(W),

R$^4$ is selected from the group consisting of CO$_2$, CO$_2$CH$_2$CO$_2$, CO$_2$CH(CH$_3$)CO$_2$, and CONHCH(X)CO$_2$, R$^5$ is selected from the group consisting of H, CH$_3$, and C$_2$H$_5$, W and X are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, OCOC$_4$N$^+$H$_9$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$3, and C$_2$SH, R$^6$ is CH(Y), R$^7$ is selected from the group consisting of C$_2$H$_4$, C$_3$H$_6$, C$_4$H$_8$, CH$_2$C$_6$H$_4$, CH$_2$CO$_2$, O, CONHCH(Z)O, CO, CO$_2$, S, CONHCH(Z)S, N, CONHCH(Z)N, CON, COCHNH(Z)CON, CONHCH(Z)CO, and CONHCH(Z)CO$_2$, R$^8$ is selected from the group consisting of OH, SH, H, CH$_3$, C$_2$H$_5$, C$_3$H$_7$, C$_4$H$_9$, CH$_2$C$_6$H$_5$, CH$_2$CHCH$_2$, and protecting groups as defined in Table 1 described in the detailed description of the present invention, Y and Z are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$H$_2$C$_6$H$_4$, OCOC$_4$N$^+$H$_9$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_r$H, [NHCH(C$_4$H$_8$NH$_2$)CO]$_r$OH, [NHCH[(CH$_2$)$_3$C(=NH)(NH$_2$)]CO]$_r$OH, and protamines, q is an integer between 1 and 20, r is an integer between 1 and 18000;

R$^{10}$ is selected from the group consisting of paclitaxel, doxorubicin, camptothecin, epirubicine, 5-fluorouracil, 10-hydroxycamptothecin, 10-aminocamptothecin, 7-ethylcamptothecin, irinotecan, methotrexate, mitomycin C, taxoid, docetaxel, chlorambucil, calicheamicin, maytansinoid, 2-pyrrolino-doxorubicin (AN-201), daunorubicin, butyric acid, melphalan, 4'-dimethyldeoxypodophyllotoxin, curcumin, podophyllotoxin, epipodophyllotoxin, 4-β-amino-4'-O-demethylepipodophyllotoxin, tallysomycin S10b, daunomycin, duocarmycin A, duocarmycin SA, cis-aconityl-daunomycin, calicheamicin, diazeniumdiolate, netropsin, 6-metcaptopurine, glucuronidation, phosmidosine, streptonigrin, hematoporphyrin, desferrioxamine (DFO), deferiprone, acivicin, estramustine, enediyne, arginine-glycin-aspatic acid peptide, neuropeptides, albumin, Bovin serum albumin (BSA), bovin pancreatic ribonuclease (RNase A), Bovin seminal ribonuclease (BS-RNase), Bowman-birk protease inhibitor (BBI), collagen, fibronetin, laminin, erythropoietin (EPO), interferon, hirudin, colony stimulating factor (CSF), insulin, desmopressin, glucagon-like peptide 1(GLP1), human growth hormone antagonist, tumor necrosis factor receptor 1(TNFR1), asparaginase, adenosine deaminase, transforming growth factor-beta (TGF-beta), bone morphogenetic proteins (BMPs), growth factors, tumor necrosis factor-related apoptosis-inducing ligand (TRAIL), cytokines, theanine, dexamethasone, heparin, chitosan, hyaluronan, cyclodextran, starch, carbohydrate, saccharide, fluorescent proteins, virus-like particle (VLP), and vaccine, a, b, c, d, e, and f respectively represent the content of each substituent, wherein a, b, and f are independently from 0.01 to 1.9, c, d, and e are independently from 0 to 1.9, and a+b+c+d+e+f=2.0, and n is from 5 to 100000.

4. The method according to claim 3, between said step (5) and step (6), further comprising a step (5-1) of dehydrogenating or de-allylesterificating the product of said step (5), when the product of said step (5) contains R$^8$ in Chemical Formula 6 selected from the group consisting of CH$_2$C$_6$H$_5$ and CH$_2$CHCH$_2$.

5. The method according to claim 3, between said step (5) and step (6), further comprising a step (5-2) of reacting the product of said step (5) with one or more selected from lysine, arginine, cystein, thiol alkylamine, polyethyleneimine, polylysine, polyarginine, and protamine.

6. A poly(organophosphazene) hydrogel containing poly (organophosphazene)-bioactive molecule conjugate of the following Chemical Formula 1 showing sol-gel phase transition with change of temperature:

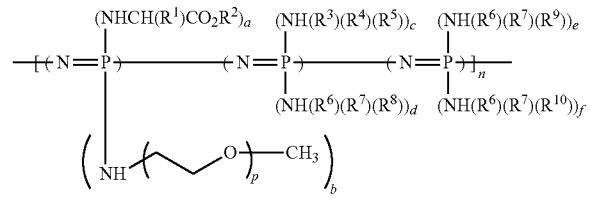

[Chemical Formula 1]

wherein, p is an integer between 7 and 50,

R$^1$ is selected from the group consisting of H, HCH$_2$, CH$_3$, CH$_2$SH, CH(CH$_3$)$_2$, CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, CH$_2$C$_2$NH$_2$C$_6$H$_4$, OCOC$_4$N$^+$H$_9$, CO$_2$C$_2$H$_5$, CH$_2$CO$_2$C$_2$H$_5$, (CH$_2$)$_2$CO$_2$C$_2$H$_5$, and HCONHCH(CH$_2$C$_6$H$_5$), $R^2$ is selected from the group consisting of $CH_3$, $C_3H_7$, $C_4H_9$, $C_2H_5$, $CH_2C_6H_5$, and $CH_2CHCH_2$, $R^3$ is $CH(W)$, $R^4$ is selected from the group consisting of $CO_2$, $CO_2CH_2CO_2$, $CO_2CH(CH_3)CO_2$, and $CONHCH(X)$ $CO_2$, $R^5$ is selected from the group consisting of H, $CH_3$, and $C_2H_5$, W and X are independently selected from the group consisting of H, $HCH_2$, $CH_3$, $CH(CH_3)_2$, $CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^6$ is $CH(Y)$, $R^7$ is selected from the group consisting of $C_2H_4$, $C_3H_6$, $C_4H_8$, $CH_2C_6H_4$, O, $CONHCH(Z)O$, CO, S, $CONHCH(Z)S$, N, $CONHCH(Z)N$, CON, $COCHNH(Z)CON$, and $CONHCH(Z)CO$, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups as defined in Table 1 described in the detailed description of the present application, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $OCOC_4N^+H_9$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_qOH$, $[NHCH[(CH_2)_3C(=NH)(NH_2)]CO]_qOH$, and protamines, q is an integer between 1 and 20, r is an integer between 1 and 18000, $R^{10}$ is selected from the group consisting of paclitaxel, doxorubicin, camptothecin, epirubicine, 5-fluorouracil, 10-hydroxycamptothecin, 10-aminocamptothecin, 7-ethylcamptothecin, irinotecan, methotrexate, mitomycin C, taxoid, docetaxel, chlorambucil, calicheamicin, maytansinoid, 2-pyrrolino-doxorubicin (AN-201), daunorubicin, butyric acid, melphalan, 4'-dimethyldeoxypodophyllotoxin, curcumin, podophyllotoxin, epipodophyllotoxin, 4-β-amino-4'-O-demethylepipodophyllotoxin, tallysomycin S10b, daunomycin, duocarmycin A, duocarmycin SA, cis-aconityl-daunomycin, calicheamicin, diazeniumdiolate, netropsin, 6-metcaptopurine, glucuronidation, phosmidosine, streptonigrin, hematoporphyrin, desferrioxamine (DFO), deferiprone, acivicin, estramustine, enediyne, arginine-glycin-aspatic acid peptide, neuropeptides, albumin, Bovin serum albumin (BSA), bovin pancreatic ribonuclease (RNase A), Bovin seminal ribonuclease (BS-RNase), Bowman-birk protease inhibitor (BBI), collagen, fibronetin, laminin, erythropoietin (EPO), interferon, hirudin, colony stimulating factor (CSF), insulin, desmopressin, glucagon-like peptide 1(GLP1), human growth hormone antagonist, tumor necrosis factor receptor 1(TNFR1), asparaginase, adenosine deaminase, transforming growth factor-beta(TGF-beta), bone morphogenetic proteins (BMPs), growth factors, tumor necrosis factor-related apoptosis-inducing ligand (TRAIL), cytokines, theanine, dexamethasone, heparin, chitosan, hyaluronan, cyclodextran, starch, carbohydrate, saccharide, fluorescent proteins, virus-like particle(VLP), and vaccine, a, b, c, d, e, and f respectively represent the content of each substituent, wherein a, b, d, and f are independently from 0.01 to 1.9, c and e are independently from 0 to 1.9, and a+b+c+d+e+f=2.0, and n is from 5 to 100000.

7. The hydrogel according to claim 6, wherein the poly (organophosphazene)-bioactive molecule conjugate is dissolved in one or more selected from the group consisting of water, buffer solution, acid solution, basic solution, salt solution, saline solution, water for injection, and glucose salt solution, and the concentration of the poly(organophosphazene))-bioactive molecule conjugate is from 1 to 50 wt. %.

8. A bioactive molecule delivery composition, containing one or more poly(organophosphazene)-bioactive molecule conjugates according to claim 1.

9. The bioactive molecule delivery composition according to claim 8, further comprising one or more selected from the group consisting of additional bioactive molecules, cells and additives.

10. The bioactive molecule delivery composition according to claim 9, wherein the content of the additive is $1 \times 10^{-6}$ to 30 wt % based on the total weight of the composition, and the additive is selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethasone, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-$Bu_4NBr$, n-$Pr_4NBr$, $Et_4NBr$, $Mg(OH)_2$, $Ca(OH)_2$, $ZnCO_3$, $Ca_3(PO_4)_2$, $ZnCl_2$, $(C_2H3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, AgCl, $AuCl_3$, $CuCl_2$, sodium tetradecyl sulfate, dodecyltrimethylammonium bromide, dodecyltrmethylammoniurn chloride, and tetradecyltrimethylammonium bromide.

11. The bioactive molecule delivery composition according to claim 9, wherein the additional bioactive molecule is selected from the group consisting of proteins, polypeptides, peptides, vaccines, genes, hormones, anti-cancer drugs, and angiogenesis inhibitors and the content of the additional bioactive molecule is from $1 \times 10^{-8}$ to 50 vol % based on the total volume of the composition.

12. The bioactive molecule delivery composition according to claim 11, wherein the protein, polypeptide, or peptide is one or more selected from the group consisting of erythropoietin (EPO), interferon-alpha, interferon-beta, interferon-gamma, growth hormone, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2(IL-2), interleukin-11(IL-11), gastrin, tetragastrin, pentagastrin, urogastrone, secretin, calcitonin, enkephalins, endorphins, angiotensins, thyrotropin releasing hormone(TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, ferment, and cytokines;

the vaccine is hepatitis vaccine;

the gene is one or more selected from the group consisting of small interference RNA (siRNA), plasmid DNA, and antisense oligodeoxynucleotide (AS-ODN);

the hormone is one or more selected from the group consisting of testosterone, estradiol, progesterone, prostaglandins and synthetic analogs thereof;

the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated protein, and synthetic analogs thereof; and the angiogenesis inhibitor is one or more selected from the group consisting of BMS-275291, Clodronate, 6-deoxy-6-demethyl-4-dedimethylaminotetracycline, Doxycycline, Marimastat, 2-Methoxyestradiol, Squalamine, SU5164, Thalidomide, TNP-470, Combretastatin A4, Soy Isoflavone, Enzastaurin, CC 5013, Celecoxib, ZD 6474, Halofuginone hydrobromide, interferon-alpha, Bevacizumab, AE-941, Interleukin-12, VEFG-trap, Cetuximab, and synthetic analogs thereof.

13. The bioactive molecule delivery composition according to claim 9, wherein the cell is one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

14. The bioactive molecule delivery composition according to claim 8, which is administered through an administration route selected from the group consisting of administration to outward intestinal tract, opthalmologically administration, injection into the cartilage tissue, bone tissue, fat tissue or cancer tissue, suction, percutaneous administration, vaginal administration, urethral administration, rectal administration, buccal administration, oral administration, pulmonary administration, ear administration, muscular administration, hypodermic administration, and intravenous administration.

15. The method according to claim 4, between said step (5-1) and step (6), further comprising a step (5-2) of reacting the product of said step (5-1) with one or more selected from lysine, arginine, cystein, thiol alkylamine, polyethyleneimine, polylysine, polyarginine, and protamine.

16. A bioactive molecule delivery composition, containing one or more hydrogels containing the poly(organophosphazene)-bioactive molecule conjugate according to claim 6.

17. The bioactive molecule delivery composition according to claim 16, further comprising one or more selected from the group consisting of additional bioactive molecules, cells and additives.

18. The bioactive molecule delivery composition according to claim 17, wherein the content of the additive is $1\times10^{-6}$ to 30 wt % based on the total weight of the composition, and the additive is selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethason, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-Bu$_4$NBr, n-Pr$_4$NBr, Et$_4$NBr, Mg(OH)$_2$, Ca(OH)$_2$, ZnCO$_3$, Ca$_3$(PO$_4$)$_2$, ZnCl$_2$, (C$_2$H3O$_2$)$_2$Zn, ZnCO$_3$, CdCl$_2$, HgCl$_2$, CoCl$_2$, (CaNO$_3$)$_2$, BaCl$_2$, MgCl$_2$, PbCl$_2$, AlCl$_3$, FeCl$_2$, FeCl$_3$, NiCl$_2$, AgCl, AuCl$_3$, CuCl$_2$, sodium tetradecyl sulfate, dodecyltrimethylammonium bromide, dodecyltrmethylammonium chloride, and tetradecyltrimethylammonium bromide.

19. The bioactive molecule delivery composition according to claim 17, wherein the additional bioactive molecule is selected from the group consisting of proteins, polypeptides, peptides, vaccines, genes, hormones, anti-cancer drugs, and angiogenesis inhibitors and the content of the additional bioactive molecule is from $1\times10^{-8}$ to 50 vol % based on the total volume of the composition.

20. The bioactive molecule delivery composition according to claim 19, wherein the protein, polypeptide, or peptide is one or more selected from the group consisting of erythropoietin (EPO), interferon-alpha, interferon-beta, interferon-gamma, growth hormone, growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2(IL-2), interleukin-11(IL-11), gastrin, tetragastrin, pentagastrin, urogastrone, secretin, calcitonin, enkephalins, endorphins, angiotensins, thyrotropin releasing hormone(TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, ferment, and cytokines;

the vaccine is hepatitis vaccine;

the gene is one or more selected from the group consisting of small interference RNA (siRNA), plasmid DNA, and antisense oligodeoxynucleotide (AS-ODN);

the hormone is one or more selected from the group consisting of testosterone, estradiol, progesterone, prostaglandins and synthetic analogs thereof;

the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated protein, and synthetic analogs thereof; and the angiogenesis inhibitor is one or more selected from the group consisting of BMS-275291, Clodronate, 6-deoxy-6-demethyl-4-dedimethylaminotetracycline, Doxycycline, Marimastat, 2-Methoxyestradiol, Squalamine, SU5164, Thalidomide, TNP-470, Combretastatin A4, Soy Isoflavone, Enzastaurin, CC 5013, Celecoxib, ZD 6474, Halofuginone hydrobromide, interferon-alpha, Bevacizumab, AE-941, Interleukin-12, VEFG-trap, Cetuximab, and synthetic analogs thereof.

21. The bioactive molecule delivery composition according to claim 17, wherein the cell is one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

22. The bioactive molecule delivery composition according to claim 16, which is administered through an administration route selected from the group consisting of administration to outward intestinal tract, opthalmologically administration, injection into the cartilage tissue, bone tissue, fat tissue or cancer tissue, suction, percutaneous administration, vaginal administration, urethral administration, rectal administration, buccal administration, oral administration, pulmonary administration, ear administration, muscular administration, hypodermic administration, and intravenous administration.

* * * * *